(12) United States Patent
Yoshimura

(10) Patent No.: US 7,978,813 B2
(45) Date of Patent: Jul. 12, 2011

(54) X-RAY CT IMAGING APPARATUS

(75) Inventor: Takahiro Yoshimura, Kyoto (JP)

(73) Assignee: J. Morita Manufacturing Corporation, Kyoto (JP)

( * ) Notice: Subject to any disclaimer, the term of this patent is extended or adjusted under 35 U.S.C. 154(b) by 86 days.

(21) Appl. No.: 12/310,647

(22) PCT Filed: May 9, 2008

(86) PCT No.: PCT/JP2008/058643
§ 371 (c)(1),
(2), (4) Date: Feb. 27, 2009

(87) PCT Pub. No.: WO2008/143032
PCT Pub. Date: Nov. 27, 2008

(65) Prior Publication Data
US 2010/0177865 A1   Jul. 15, 2010

(30) Foreign Application Priority Data
May 11, 2007   (JP) ................................ 2007-126821

(51) Int. Cl.
*A61B 6/14* (2006.01)
(52) U.S. Cl. ........................................................ 378/38
(58) Field of Classification Search .............. 378/38–40, 378/195–197
See application file for complete search history.

(56) References Cited

U.S. PATENT DOCUMENTS

| 5,692,027 | A | | 11/1997 | Yoshimura et al. | ............. 378/38 |
| 6,118,842 | A | * | 9/2000 | Arai et al. | ........................ 378/39 |
| 2005/0031086 | A1 | | 2/2005 | Dalpiaz | ......................... 378/195 |

FOREIGN PATENT DOCUMENTS

| JP | H7-327985 | 12/1995 |
| JP | 2002-219127 | 8/2002 |
| JP | 2002-315746 | 10/2002 |
| JP | 2004-329293 A | 11/2004 |
| JP | 2006-130037 A | 5/2006 |
| JP | 2006-288726 A | 10/2006 |
| JP | 2006-314339 A | 11/2006 |
| JP | 2006-314774 | 11/2006 |
| WO | WO 2006/109808 A | 10/2006 |
| WO | WO 2007/046372 | 4/2007 |

* cited by examiner

*Primary Examiner* — Courtney Thomas
(74) *Attorney, Agent, or Firm* — DLA Piper LLP (US)

(57) ABSTRACT

An x-ray CT imaging apparatus emits an x-ray cone beam to an object to generate an x-ray CT image on the basis of a transmission x-ray which is transmitted through the object. An image generation part generates an image obtained by superposing an imaging object region display on a position setting image representing the object and displays the image on a display part. The image generation part changes the imaging object region display in accordance with an x-ray CT imaging mode selected by an imaging mode selection part.

7 Claims, 20 Drawing Sheets

F I G. 1
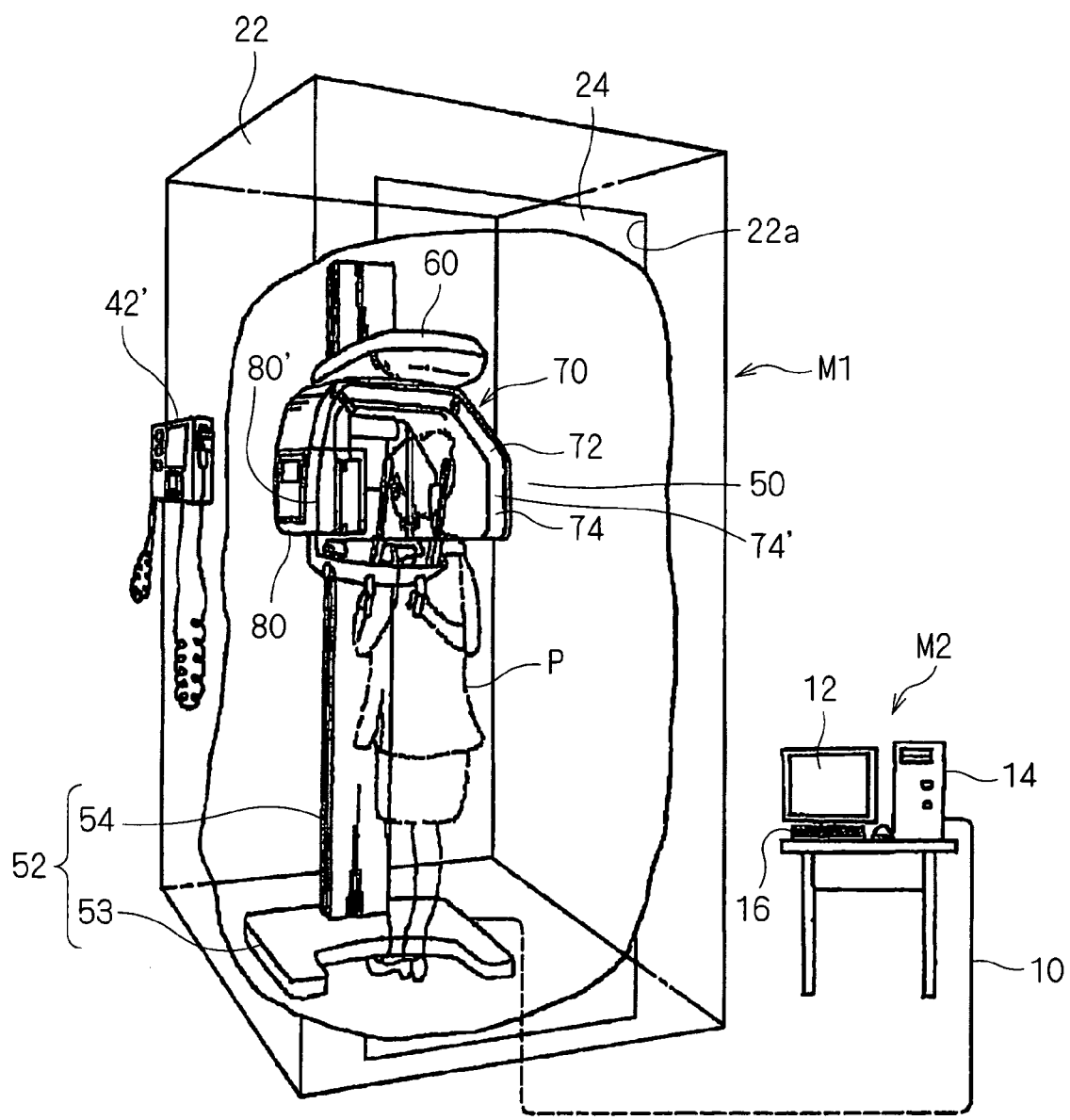

F I G . 3
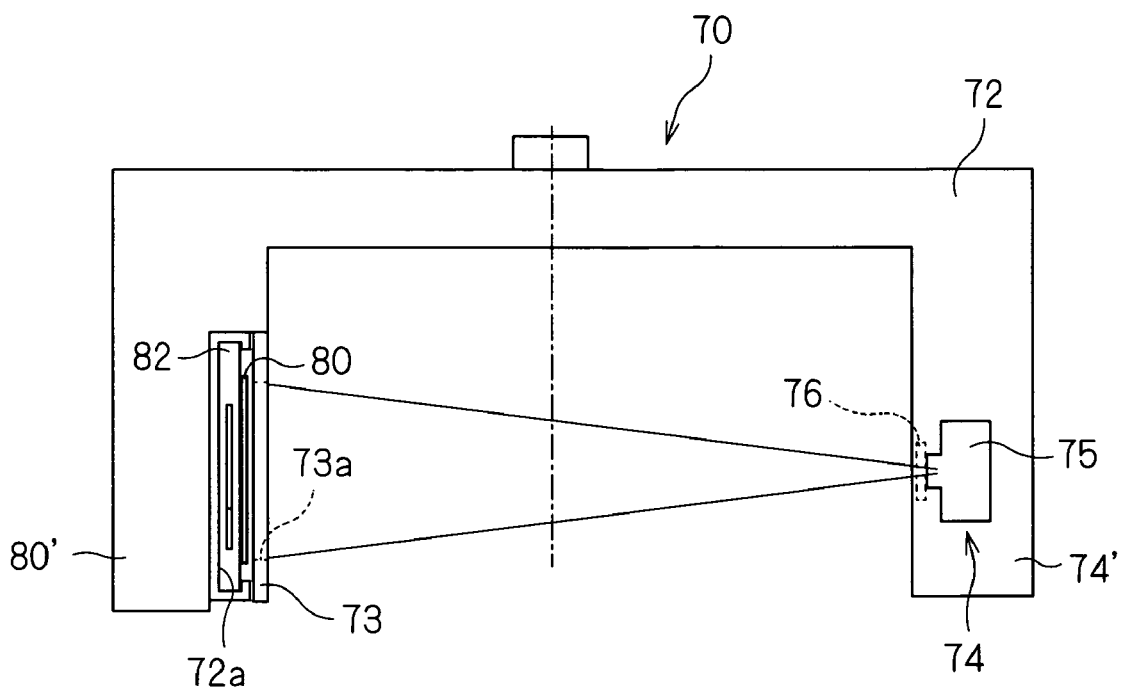

F I G. 1 1
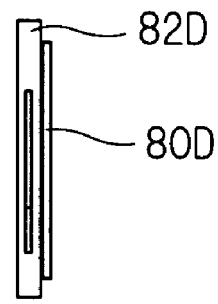
F I G. 1 2
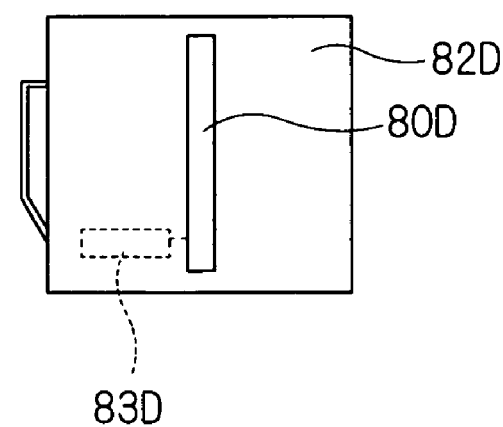

F I G. 2 4
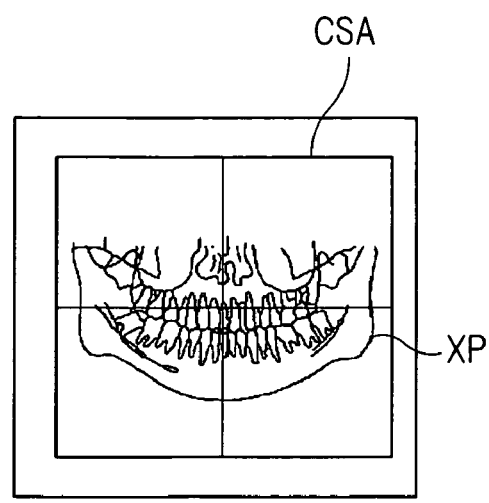
F I G. 2 5
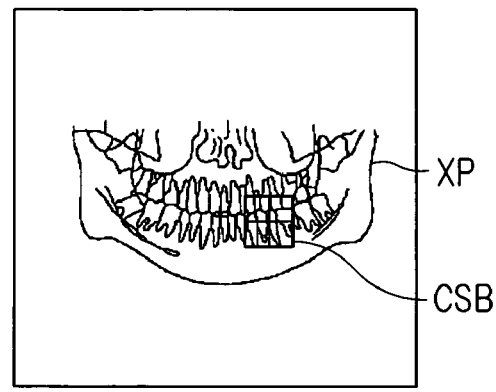
F I G. 2 6
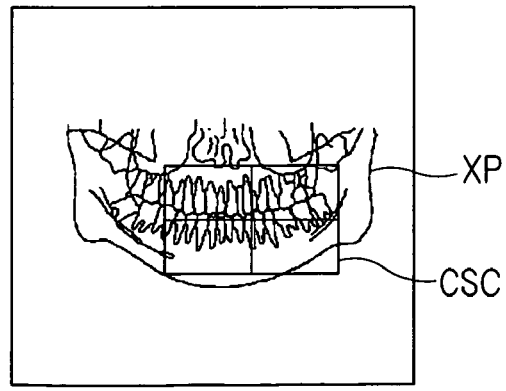

X-RAY CT IMAGING APPARATUS

TECHNICAL FIELD

The present invention relates to a technique of emitting x-ray radiation to a object and forming an image on the basis of a transmission x-ray which is transmitted through the object in the medical field and the like, and more particularly to a technique of performing radiography in a particular mode selected among a plurality of x-ray CT imaging modes.

BACKGROUND ART

This type of conventional x-ray CT imaging apparatuses are disclosed in Patent Document 1 and Patent Document 2.

Patent Document 1 discloses a technique in which a schematic view of object, representing a modeled object, and an x-ray imaging target region are displayed on a display means and the position of the x-ray imaging target region is set while the relatively positional relation of the x-ray imaging target region with respect to the schematic view of object is observed.

Patent Document 2 discloses a technique in which a scout view image which is a wide-range view of an object is obtained and a desired imaging object region is set with the scout view image.

Patent Document 1: Japanese Patent Application Laid Open Gazette No. 2002-315746.

Patent Document 2: Japanese Patent Application Laid Open Gazette No. 2006-314774.

DISCLOSURE OF INVENTION

In recent years, an x-ray imaging apparatus is proposed, which is capable of performing radiography in a particular mode selected among a plurality of x-ray CT imaging modes with imaging regions of different shapes and the like. In order to allow radiography in various imaging modes in an imaging apparatus, a configuration to change the radiation range of x-ray beams in accordance with any one x-ray CT imaging mode is proposed.

In such an x-ray imaging apparatus capable of performing radiography in a plurality of x-ray CT imaging modes as above, however, the imaging object region differs depending on the imaging mode. This makes it necessary to change a display of the imaging object region to be used for positioning in accordance with the imaging mode.

Therefore, it is an object of the present invention to easily change an imaging object region display to be used for positioning in accordance with the x-ray CT imaging mode.

In order to solve the above problem, the present invention is intended for an x-ray CT imaging apparatus for emitting an x-ray cone beam to an object to generate an x-ray CT image on the basis of a transmission x-ray which is transmitted through the object. According to a first aspect of the present invention, the x-ray CT imaging apparatus includes an x-ray generator, an x-ray image sensor provided oppositely to the x-ray generator with the object interposed therebetween, for outputting x-ray projection data in accordance with a transmission x-ray which is transmitted through the object, an imaging mode selection part for performing mode selection from a plurality of x-ray CT imaging modes with x-ray CT imaging regions of different shapes, an image generation part capable of generating an x-ray CT image in accordance with the x-ray CT imaging mode selected by the imaging mode selection part on the basis of the x-ray projection data outputted from the x-ray image sensor and capable of generating an image obtained by superposing an imaging object region display on a position setting image representing the object, an operation part for receiving an operation for moving the imaging object region display relatively to the position setting image, a moving mechanism part for positioning the x-ray generator and the x-ray image sensor relatively to the object in accordance with the position of the imaging object region display, and a display part for displaying an image generated by the image generation part, and in the x-ray CT imaging apparatus, the image generation part changes the imaging object region display in accordance with the x-ray CT imaging mode selected by the imaging mode selection part.

Since the image generation part thereby changes the imaging object region display in accordance with the x-ray CT imaging mode selected by the imaging mode selection part, it is possible to easily change the imaging object region display to be used for positioning in accordance with the imaging mode, and this makes it easier for an operator and the like to perform positioning.

According to a second aspect of the present invention, the x-ray CT imaging apparatus for emitting an x-ray cone beam to an object to generate an x-ray CT image on the basis of a transmission x-ray which is transmitted through the object, includes an x-ray generator, an x-ray image sensor provided oppositely to the x-ray generator with the object interposed therebetween interchangeably or switchably, for outputting x-ray projection data in accordance with a transmission x-ray which is transmitted through the object, a mode signal output part for outputting an imaging mode signal for one of a plurality of x-ray CT imaging modes with x-ray CT imaging regions of different shapes, in accordance with the interchange or switch of the x-ray image sensor, an image generation part capable of generating an x-ray CT image in accordance with the x-ray CT imaging mode selected by the imaging mode signal on the basis of the x-ray projection data outputted from the x-ray image sensor and capable of generating an image obtained by superposing an imaging object region display on a position setting image representing the object, an operation part for receiving an operation for moving the imaging object region display relatively to the position setting image, a moving mechanism part for positioning the x-ray generator and the x-ray image sensor relatively to the object in accordance with the position of the imaging object region display, and a display part for displaying an image generated by the image generation part, and in the x-ray CT imaging apparatus, the image generation part changes the imaging object region display in accordance with the x-ray CT imaging mode selected by the imaging mode signal.

By interchanging or switching the x-ray image sensor in accordance with the x-ray CT imaging mode, the imaging object region display can be changed, and this makes it unnecessary to perform any operation for mode selection other than the interchange or switch of the x-ray image sensor.

Herein, a case where the imaging object region display is changed in accordance with the x-ray CT imaging mode refers to a case where it is changed relatively to the position setting image, and therefore the case includes a case where the size and the like of the imaging object region display is changed while the size and the like of the position setting image displayed on the display part is kept substantially constant and another case where the position setting image is displayed, being reduced or enlarged, while the size and the like of the imaging object region display displayed on the display part is kept substantially constant.

The configuration of the present invention is particularly effective in a case where mode selection is performed out of a plurality of x-ray CT imaging modes with radiation fields of different shapes in a field of medical x-ray CT for maxillofacial region in dentistry, otolaryngology, ophthalmology and the like.

Further, the present invention can be also widely used in fields of industrial x-ray CT and like, not only in the field of medical x-ray CT.

These and other objects, features, aspects and advantages of the present invention will become more apparent from the following detailed description of the present invention when taken in conjunction with the accompanying drawings.

BRIEF DESCRIPTION OF DRAWINGS

FIG. 1 is a schematic view showing an overall structure of an x-ray CT imaging apparatus in accordance with a preferred embodiment;

FIG. 3 is an illustration of an imaging unit body;

FIG. 11 is a side elevation showing a cassette prepared for a panoramic imaging mode;

FIG. 12 is an elevation view showing the cassette prepared for the panoramic imaging mode;

FIG. 24 is a view showing an exemplary position setting screen used for radiography in the x-ray CT imaging mode for large radiation field;

FIG. 25 is a view showing an exemplary position setting screen used for radiography in the local x-ray CT imaging mode for small radiation field;

FIG. 26 is a view showing an exemplary position setting screen used for radiography in the local x-ray CT imaging mode for medium radiation field;

BEST MODE FOR CARRYING OUT THE INVENTION

Hereinafter, an x-ray CT imaging apparatus of the preferred embodiment will be described. In this preferred embodiment, discussion will be made on a case where the object is human teeth.

<Overall Structure>

Figure 2:
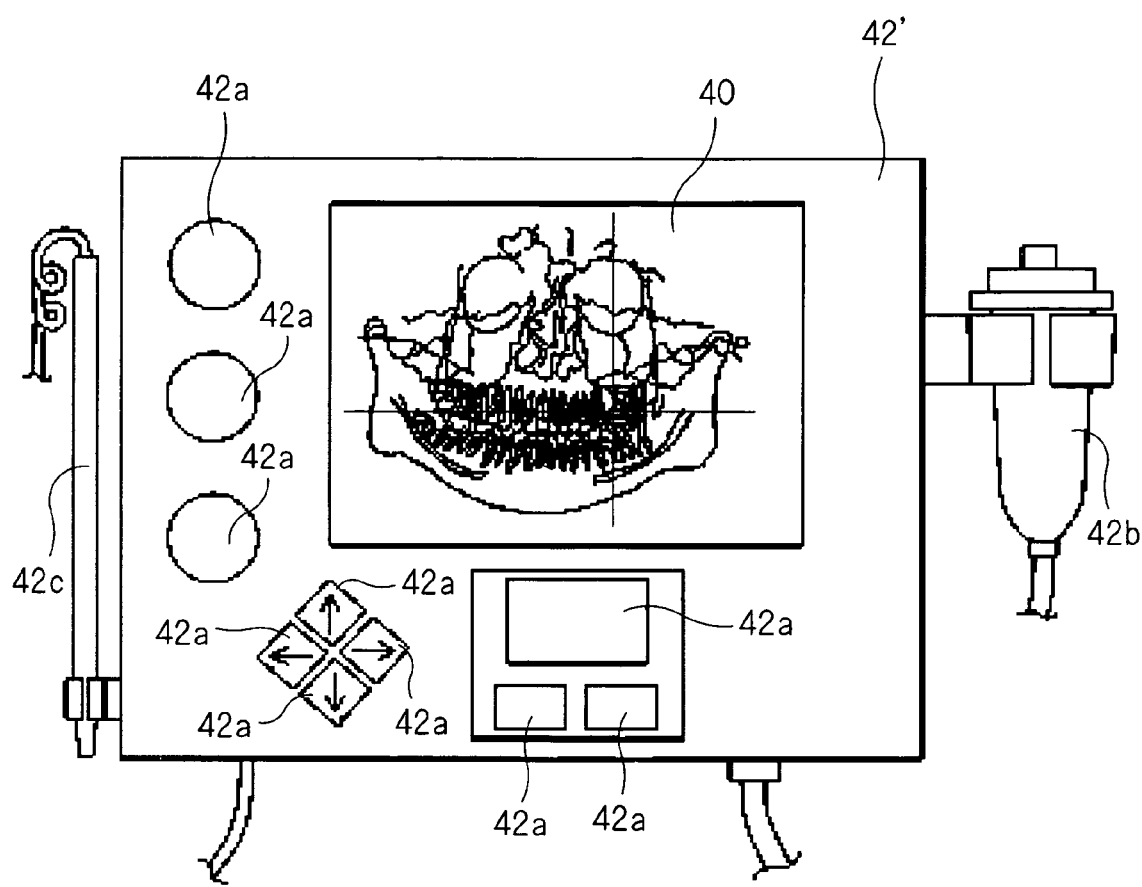
FIG. 2 is a view showing an imaging unit body-side control part in the x-ray CT imaging apparatus.

FIG. 1 is a schematic view showing an overall structure of an x-ray CT imaging apparatus in accordance with the preferred embodiment, and FIG. 2 is a view showing an imaging unit body-side control part 30 in the x-ray CT imaging apparatus.

This x-ray CT imaging apparatus is an apparatus which emits an x-ray cone beam to an object to generate an x-ray CT (computerized tomography) image on the basis of a transmission x-ray which is transmitted through the object. Herein, the x-ray CT imaging apparatus can not only generate an x-ray CT image but also emit an x-ray slit beam and the like to generate an x-ray image which is obtained by x-ray transmission radiography of a row of teeth from a predetermined direction (e.g., from the front or the side of the row of teeth), a panoramic x-ray image which is obtained by x-ray transmission radiography of a whole row of teeth along a dental arch, and the like.

This x-ray CT imaging apparatus comprises an x-ray CT imaging unit body M1 and an x-ray image display unit M2.

The x-ray image display unit M2 is formed of a general computer having a display part 12 such as a liquid crystal display (LCD) or the like, a computer-side control part 14 and an operation part 16 such as a keyboard, a mouse and the like. The x-ray image display unit M2 performs a predetermined operation for generating an image on the basis of an image signal or the like transmitted mainly from the x-ray CT imaging unit body M1. The details of the operation will be discussed later.

The x-ray CT imaging unit body M1 is disposed inside an x-ray proof chamber 22 and comprises a control panel 42' attached to an outer wall of the x-ray proof chamber 22 and an x-ray imaging part 50 provided inside the x-ray proof chamber 22.

The x-ray proof chamber 22 has a box-like shape of substantially rectangular parallelepiped, being capable of housing a person P therein, and the person P can come in and go out through a gate 22a provided with a door 24.

The control panel 42' has a substantially box-like outer shape and is attached to a side outer surface of the above x-ray proof chamber 22. This control panel 42' is provided with a display part 40 and an operation part 42. The display part 40 is formed of a liquid crystal display (LCD) or the like, being capable of displaying a screen for command from the x-ray CT imaging apparatus, information on radiography result and the like. The operation part 42 has various switches 42a, an imaging switch 42b, a touch pen 42c for inputting coordinate indication to the display part 40, and the like and receives various commands for the x-ray CT imaging unit body M1. For coordinate indication input, not only the touch pen 42c, but also, e.g., switches for numerical input and the like may be used. Further, a touch panel may be incorporated in the display part 40 to serve as an operation part.

In the x-ray imaging part 50 inside the x-ray proof chamber 22, the imaging unit body-side control part 30 which is not shown in FIG. 1 is included. This imaging unit body-side control part 30 mainly controls the above x-ray imaging part 50 to perform an imaging operation and the like, and the details of the operation will be discussed later.

The x-ray imaging part 50 has a stand 52, a moving mechanism part 60 and an imaging unit body 70.

The stand 52 has a foot 53 placed on a bottom surface of the x-ray proof chamber 22 and a column 54 supported by the foot 53, being stood, and the height of the column 54 is set somewhat higher than the height of a person P.

The moving mechanism part 60 is attached to an up-and-down moving part 61 which is movable up and down with respect to the column 54 of the stand 52 and supports the imaging unit body 70 rotatably at the level of the head of a standing person P.

Further, the moving mechanism part 60 supports the imaging unit body 70 movably and has a configuration to move the imaging unit body 70 with respect to the object in such a manner as discussed later.

Herein, the moving mechanism part 60 has an X-Y moving mechanism part for moving the imaging unit body 70 two-dimensionally in a horizontal plane and a rotation driving part for rotating the imaging unit body 70 around a vertical axis. The X-Y moving mechanism part consists of an X-axis motor 60x and a Y-axis motor 60y discussed later. The X-Y moving mechanism part and the rotation driving part are each formed of a well-known driving mechanism which is a combination of an actuator such as a motor and the like, a powertrain mechanism such as a gear and a linkage mechanism and the like, and therefore detailed description thereof will be omitted. As to the moving mechanism part 60, for convenience of discussion, it is assumed that a direction parallel to the vertical axis about which the imaging unit body 70 rotates, i.e., a vertical direction of this figure is a Z-axis direction, the left and right direction substantially orthogonal to the Z-axis, as viewed from one who comes in from the gate and faces the x-ray imaging part 50, is an X-axis direction and a direction substantially orthogonal both to the Z-axis and to the X-axis is a Y-axis direction. The moving mechanism part 60 is provided with a Z moving mechanism part for moving the imaging unit body 70 in the Z-axis direction. In FIG. 1, a Z-axis motor 60z described later, which is a constituent element of the Z moving mechanism part is provided inside the up-and-down moving part 61, and the up-and-down moving part 61 is moved up and down by the drive of the Z-axis motor 60z to move the imaging unit body 70 up and down, which is supported by the moving mechanism part 60 attached to the up-and-down moving part 61.

Then, in a state where the imaging unit body 70 has moved to a predetermined position in accordance with a selected imaging mode, the imaging unit body 70 can be rotated in an orbit in accordance with the imaging mode.

The up-and-down moving part 61 may be provided with a holding part 62 which is vertically movable together with the moving mechanism part 60. The holding part 62 is a part for holding the object and has a chin rest for resting a chin thereon, an ear rod for sandwiching ears, and the like. By pressing the chin, the head and the like of the person P against the holding part 62, the dentomaxillofacial region and the like, which is the object, can be positioned at a predetermined position suitable for radiography with respect to the imaging unit body 70. The holding part 62 may be moved by the moving mechanism part 60. Specifically, the chin rest, the ear rod and the like may be driven by the not-shown X-Y moving mechanism part which moves the chin rest, ear rod and the like two-dimensionally in the horizontal plane by the X-axis motor 60x and the Y-axis motor 60y described later and the not-shown Z moving mechanism part which moves the chin rest, the ear rod and the like in the Z-axis direction by the Z-axis motor 60z described later. In the case of FIG. 1, the X-Y moving mechanism part and the Z moving mechanism part are provided between the up-and-down moving part 61 and the chin rest, the ear rod and the like.

As discussed above, it is thought that, as the moving mechanism part 60, there are a part of the moving mechanism part 60 on the side of the imaging unit body 70, which moves the imaging unit body 70, and the other part of the moving mechanism part 60 on the side of the holding part 62, which moves the holding part 62. Either the part of the moving mechanism part 60 on the side of the imaging unit body 70 or the part of the moving mechanism part 60 on the side of the holding part 62 has only to be provided but both of these parts may be provided. In a case where both the part of the moving mechanism part 60 on the side of the imaging unit body 70 and the part of the moving mechanism part 60 on the side of the holding part 62 are provided, the part of the moving mechanism part 60 on the side of the imaging unit body 70 and the part of the moving mechanism part 60 on the side of the holding part 62 may be driven independently from each other or may be interlocked.

Though the part of the moving mechanism part 60 on the side of the imaging unit body 70 supports the imaging unit body 70, it is also thought, as viewed from the imaging unit body 70, that the imaging unit body 70 has the part of the moving mechanism part 60 on the side of the imaging unit body 70, which moves the imaging unit body 70 itself.

The same applies to the part of the moving mechanism part 60 on the side of the holding part 62, and it is also thought, as viewed from the holding part 62, that the holding part 62 has the part of the moving mechanism part 60 on the side of the holding part 62, which moves the holding part 62 itself.

The imaging unit body 70 has a rotation arm 72 of substantially inverted U-shape, an x-ray generator 74 provided inside an x-ray generation part 74' which is an end portion of the rotation arm 72 and an x-ray image sensor 80 provided in an x-ray detection part 80'. The x-ray generator 74 has a configuration to emit x-ray beams toward the object. The x-ray image sensor 80 is disposed oppositely to the x-ray generator 74 with the object interposed therebetween and has a configuration to receive a transmission x-ray which is transmitted through the object and output x-ray projection data in accordance with the transmission x-ray.

The imaging unit body 70 is moved in an orbit in accordance with the imaging mode, the x-ray generator 74 emits x-ray beams and the x-ray image sensor 80 receives the transmission x-ray which is transmitted through the object, and the x-ray projection data in accordance with the transmission x-ray is thereby outputted. Then, on the basis of the x-ray projection data, an x-ray image in accordance with the imaging mode is generated.

<Imaging Unit Body>

Figure 4:
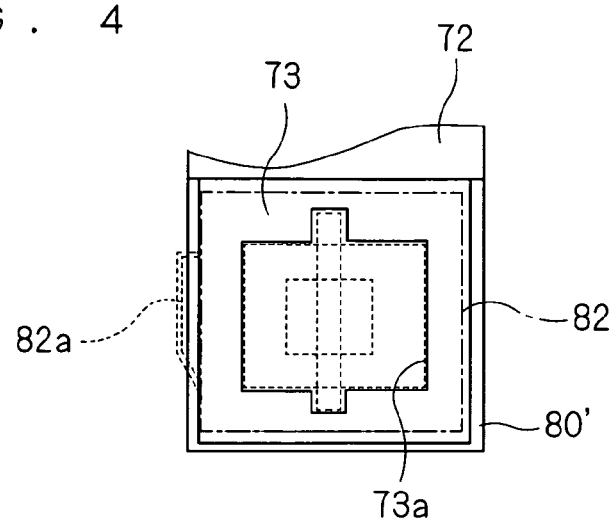
FIG. 4 is a view showing an end portion of the imaging unit body.

Detailed description will be made on the imaging unit body 70. FIG. 3 is an illustration of the imaging unit body 70, and FIG. 4 is a view showing the x-ray detection part 80' of the imaging unit body 70.

In the x-ray detection part 80' of the rotation arm 72, a cassette holder 72a and a shield member 73 are provided, and a cassette 82 having the x-ray image sensor 80 is inserted removably into the cassette holder 72a.

The cassette 82 has a flat and substantially box-like shape and on its one main surface, the x-ray image sensor 80 is attached. For various imaging modes, a plurality of cassettes 82 are prepared, being interchangeable to be inserted into the cassette holder 72a. On one side portion of the cassette 82, a grip 82a is provided. The configuration to serve in accordance with the imaging modes will be discussed next.

The cassette holder 72a has a flat holding space which is open on one side portion of the rotation arm 72 (on the frontward side of FIG. 3, the left of FIG. 4), by which the above cassette 82 can be held, and on the upper and lower side portions, insertion grooves extending backward from the opening is formed. Then, by putting the cassette 82 into the cassette holder 72a with its upper and lower side portions being fitted in the insertion grooves, the cassette 82 is held at a predetermined position inside the cassette holder 72a with its x-ray image sensor 80 facing the x-ray generator 74.

The configuration to allow the cassette 82 to be removable and interchangeable is not limited to the above example. There may be a configuration, for example, where insertion grooves are provided at both side portions of the cassette holder and an opening is provided at a lower end portion thereof, to allow the cassette 82 to be inserted therein and removed therefrom. Further, it is not always necessary to guide the cassette 82 with the insertion grooves for insertion and removal.

The above shield member 73 is provided on a side of the cassette holder 72a which faces to the x-ray generator 74. The shield member 73 is formed of a plate material capable of blocking off the x-ray beams, and an opening 73a is provided at a substantially central portion thereof. When the x-ray beams are emitted in various manners discussed later, the shield member 73 serves to allow the x-ray beams to pass through in a maximum region required for radiography and inhibit the x-ray beams to pass through in the remaining region. Herein, the opening 73a is formed in a shape obtained by overlaying a radiation region of x-ray cone beam in an x-ray CT imaging mode for large radiation field discussed later on a radiation region of x-ray slit beam in a panoramic imaging mode or the like. In FIG. 4, a substantially quadrate frame indicated by the dotted line inside the opening 73a represents the radiation region of the x-ray beams in various imaging modes.

Discussion will be made on a plurality of cassettes 82 prepared in accordance with various imaging modes. In the following discussion, when described regardless of the imaging modes, the cassette, the x-ray image sensor and the information processing part are generically designated by reference numerals 82, 80 and 83, respectively, and when described by imaging modes, these elements are designated by reference signs 82A, 82B, 82C and 82D, 80A 80B, 80C and 80D, and 83A, 83B, 83C and 83D, respectively.

Figure 5:
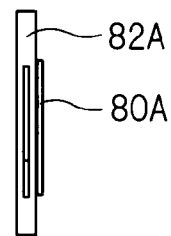
FIG. 5 is a side elevation showing a cassette prepared for an x-ray CT imaging mode for large radiation field.
Figure 6:
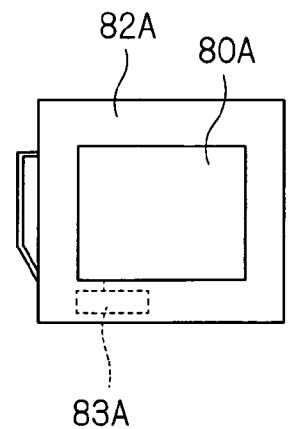
FIG. 6 is an elevational view showing the cassette prepared for the x-ray CT imaging mode for large radiation field.

FIGS. 5 and 6 are views each showing a cassette 82A prepared for the x-ray CT imaging mode for large radiation field. FIG. 5 is a side elevation of the cassette 82A, and FIG. 6 is an elevational view of the cassette 82A.

This cassette 82A comprises an x-ray image sensor 80A and an information processing part 83A used for the x-ray CT of the large radiation field. When the cassette 82A is inserted into the cassette holder 72a, the information processing part 83A gets connected intercommunicably to a control part 110 (see FIG. 19) including the computer-side control part 14 and the imaging unit body-side control part 30 through a not-shown connector and the like.

The x-ray image sensor 80A is attached to one main surface of the cassette 82A and has a substantially quadrate detection surface. In the x-ray CT imaging mode for large radiation field, the x-ray generator 74 emits an x-ray cone beam of substantially quadrangular pyramid, which is capable of emitting x-ray radiation to a whole object, i.e., a whole head, a whole chin or the like. The x-ray image sensor 80A has a substantially quadrate detection surface which is capable of detecting such a relatively wide-range x-ray cone beam and outputs x-ray projection data in accordance with a transmission x-ray of the x-ray cone beam.

The information processing part 83A is formed of a general-type microcomputer including a CPU, a ROM, a RAM and the like and performs predetermined processing in accordance with a software program stored in advance.

Herein, the information processing part 83A performs driving control of the x-ray image sensor 80A on the basis of a driving command from the control part 110, and also performs amplification, A/D conversion or the like on a signal outputted from the x-ray image sensor 80A to output the processed signal to the control part 110.

The information processing part 83A has a storage part which is capable of storing type identifying information on the type of the cassette 82A, more specifically, type identifying information indicating that the cassette 82A is intended for use in the x-ray CT imaging mode for large radiation field and has a configuration to output the type identifying information to the control part 110. The type identifying information is outputted when the cassette 82A is set into the cassette holder 72a or the like. In other words, the information processing part 83 serves as a mode signal output part for outputting an imaging mode signal in accordance with the imaging mode changed by the interchange of the x-ray image sensor 80 or the like.

The information processing part 83A may have a function of further outputting various information such as radiation field range information of the x-ray image sensor 80, information on the voltage and current for the detection, use period information, use count information and the like.

Figure 7:
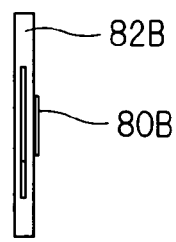
FIG. 7 is a side elevation showing a cassette prepared for an x-ray CT imaging mode for small radiation field.
Figure 8:
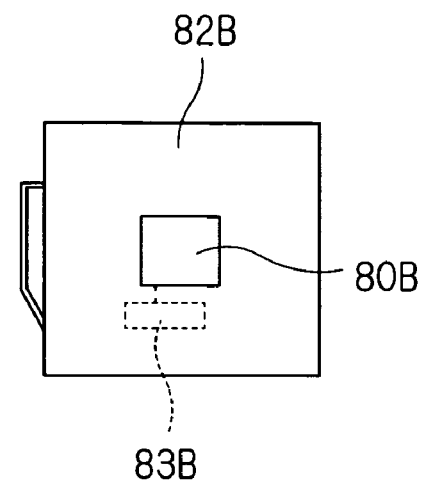
FIG. 8 is an elevational view showing the cassette prepared for the x-ray CT imaging mode for small radiation field.

FIGS. 7 and 8 are views showing a cassette 82B prepared for the x-ray CT imaging mode for small radiation field. FIG. 7 is a side elevation of the cassette 82B, and FIG. 8 is an elevational view of the cassette 82B.

Like the above cassette 82A, this cassette 82B comprises an x-ray image sensor 80B and an information processing part 83B.

The cassette 82B is different from the cassette 82A in that the detection surface of the x-ray image sensor 80B is a relatively narrow region of substantial quadrate for the x-ray CT of the small radiation field. Specifically, in the x-ray CT imaging mode for small radiation field, emitted is the x-ray cone beam of substantially quadrangular pyramid, which is capable of emitting x-ray radiation to a relatively narrow region (the narrowest region in the present apparatus) such as a specified tooth or the like. The x-ray image sensor 80B has a substantially quadrate detection surface which is capable of detecting such a narrow-range x-ray cone beam.

Figure 9:
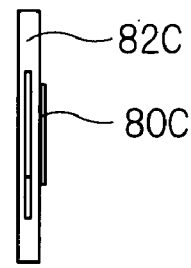
FIG. 9 is a side elevation showing a cassette prepared for an x-ray CT imaging mode for medium radiation field.
Figure 10:
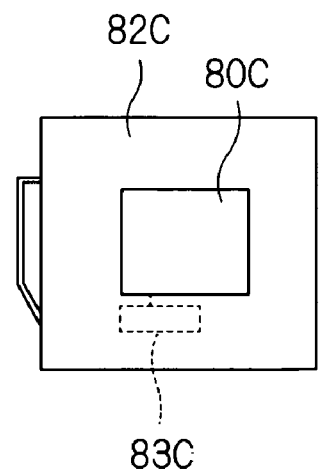
FIG. 10 is an elevational view showing the cassette prepared for the x-ray CT imaging mode for medium radiation field.

FIGS. 9 and 10 are views each showing a cassette 82C prepared for the x-ray CT imaging mode for medium radiation field. FIG. 9 is a side elevation of the cassette 82C, and FIG. 10 is an elevational view of the cassette 82C.

Like the above cassette 82A, this cassette 82C comprises an x-ray image sensor 80C and an information processing part 83C.

The cassette 82C is different from the cassette 82A in that the detection surface of the x-ray image sensor 80C is a medium-sized region of substantial quadrate for the x-ray CT of the medium radiation field. Specifically, in the x-ray CT imaging mode for medium radiation field, emitted is the x-ray cone beam of substantially quadrangular pyramid, which is capable of emitting x-ray radiation to a medium-sized region between the regions in the cases of the cassettes 82A and 82B such as specified teeth or the like. The x-ray image sensor 80C has a substantially quadrate detection surface which is capable of detecting such a medium-range x-ray cone beam.

FIGS. 11 and 12 are views each showing a cassette 82D prepared for the panoramic imaging mode. FIG. 11 is a side elevation of the cassette 82D, and FIG. 12 is an elevational view of the cassette 82D.

Like the above cassette 82A, this cassette 82D comprises an x-ray image sensor 80D and an information processing part 83D.

The cassette 82D is different from the cassette 82A in that the detection surface of the x-ray image sensor 80D is a substantially vertical rectangular region for the panoramic radiography. Specifically, in the panoramic imaging mode, an x-ray slit beam is emitted. The x-ray image sensor 80D has a substantially vertical rectangular detection surface which is capable of detecting such an x-ray slit beam.

Further, the cassettes 82A, 82B, 82C and 82D each have the substantially same outer shape and can be selectively inserted into the cassette holder 72a. The information processing parts 83A, 83B, 83C and 83D provided therein serve as mode signal output parts for outputting type identifying information on their own types, i.e., type identifying information indicating that the cassettes are intended for use in the x-ray CT imaging mode for large radiation field, in the x-ray CT imaging mode for small radiation field, in the x-ray CT imaging mode for medium radiation field and in the panoramic imaging mode, respectively.

The mode signal output part does not always need to be provided in each of the cassettes 82A, 82B, 82C and 82D but may be provided in any portion. There may be a configuration, for example, where the cassettes 82A, 82B, 82C and 82D are each provided with a specific identification element and a mode signal output part capable of determining the identification element is provided in, e.g., the cassette holder 72a. The identification element may be a cut which has a different shape depending on the cassette, a bar code or an IC tag which is different depending on the cassette, or the like. In any case, the mode signal output part determines each identification element and outputs an imaging mode signal for each cassette.

Figure 13:
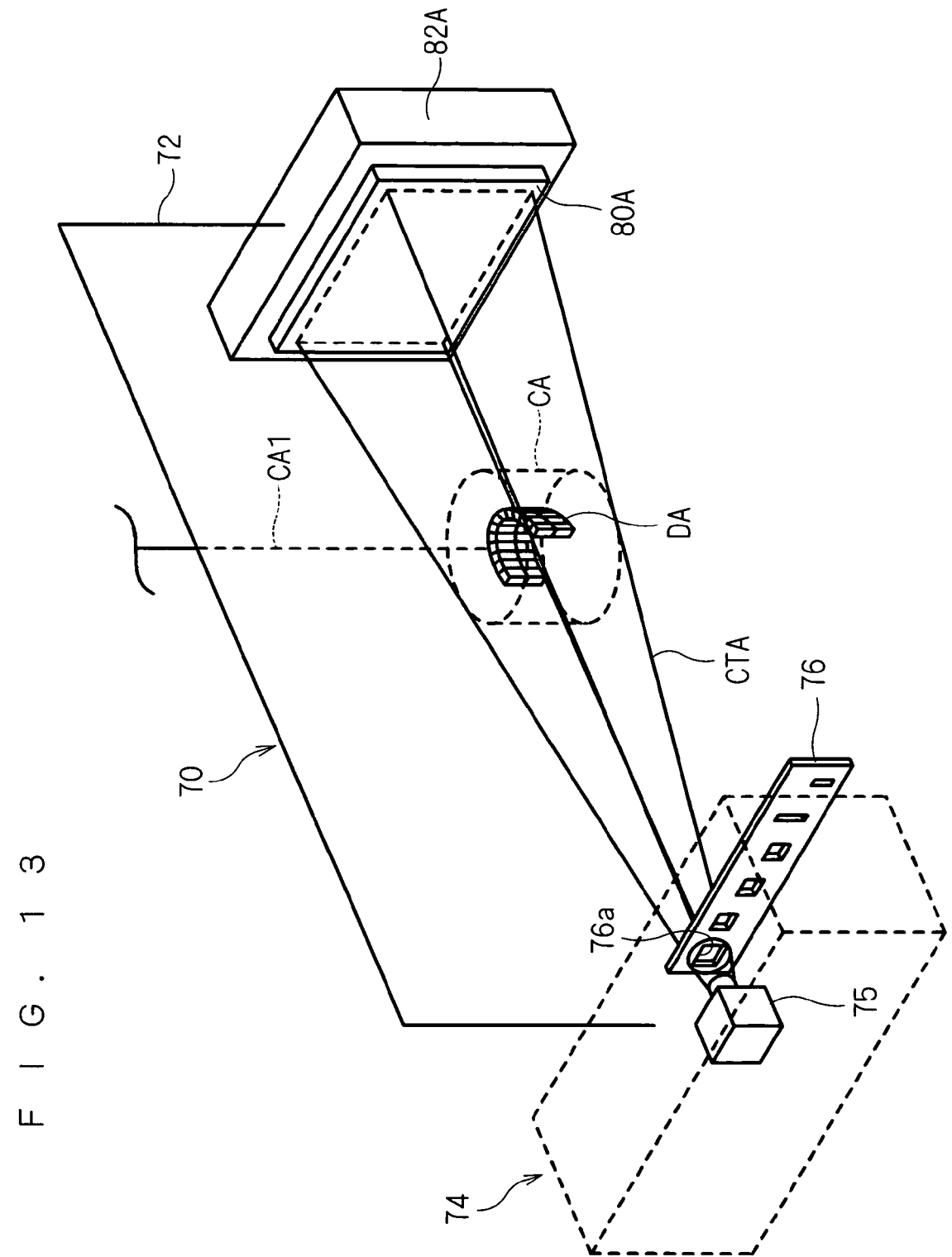
FIG. 13 is an illustration of a state where CT of the large radiation field is performed.

FIG. 13 is an illustration of a state where the x-ray CT of the large radiation field is performed. As shown in FIGS. 3 and 13, the x-ray generator 74 has an x-ray generator body 75 and a shield member 76 provided on a radiation direction side of the x-ray generator body 75. The x-ray generator body 75 has a configuration to emit an x-ray cone beam having a spread wider than the spread enabling the x-ray CT of the large radiation field. The shield member 76 has at least an opening 76a for the x-ray CT of the large radiation field, an opening 76b for the x-ray CT of the small radiation field, an opening 76c for the x-ray CT of the medium radiation field and an opening 76d for the panoramic radiography. In the exemplary case of FIG. 13, the opening 76b includes three openings having different heights in the Z-axis direction.

Then, by changing the positions of the openings 76a, 76b, 76c and 76d provided to the front of the x-ray generator body 75 in the radiation direction, the x-ray cone beam is limited to an appropriate radiation range for the imaging mode. The shield member 76 can be moved by a not-shown moving mechanism, to provide one of the openings 76a, 76b, 76c and 76d in accordance with the imaging mode to the front of the x-ray generator body 75 in the radiation direction on the basis of an instruction from the control part 110 discussed later. The openings 76a, 76b, 76c and 76d do not always need to each have a rectangular shape but may each have a rectangular shape with round corners, or the openings 76a, 76b and 76c may have a substantially circular shape or the like.

Figure 14:
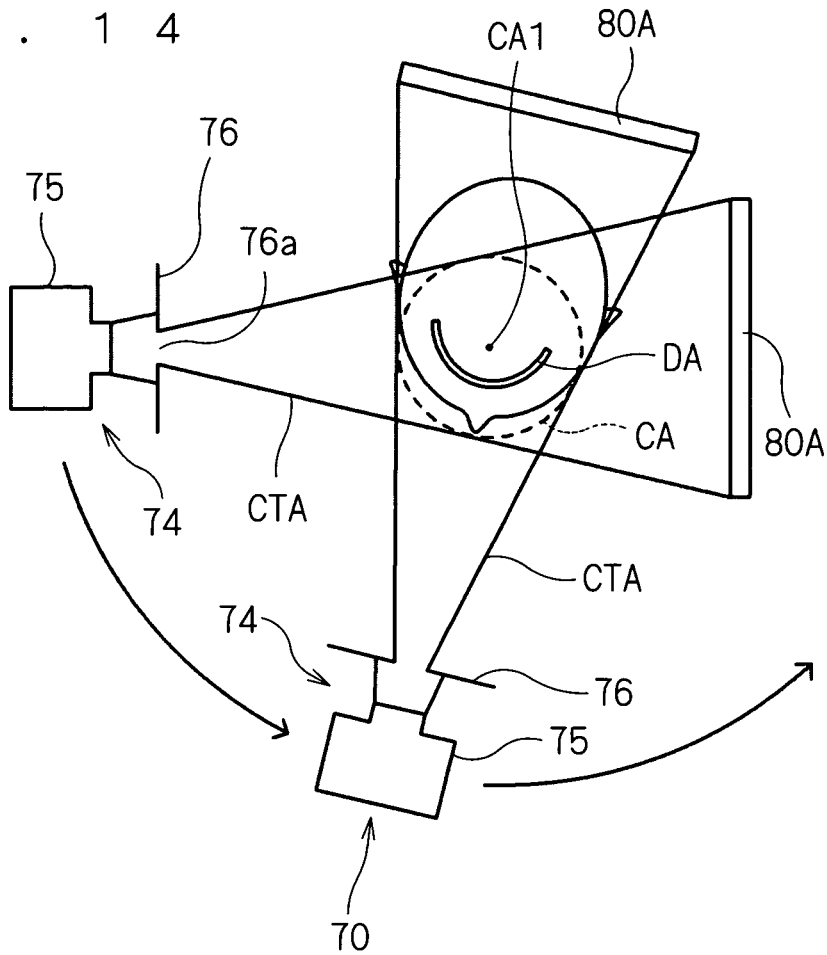
FIG. 14 is an illustration of a state of movement in performing the CT of the large radiation field.
Figure 15:
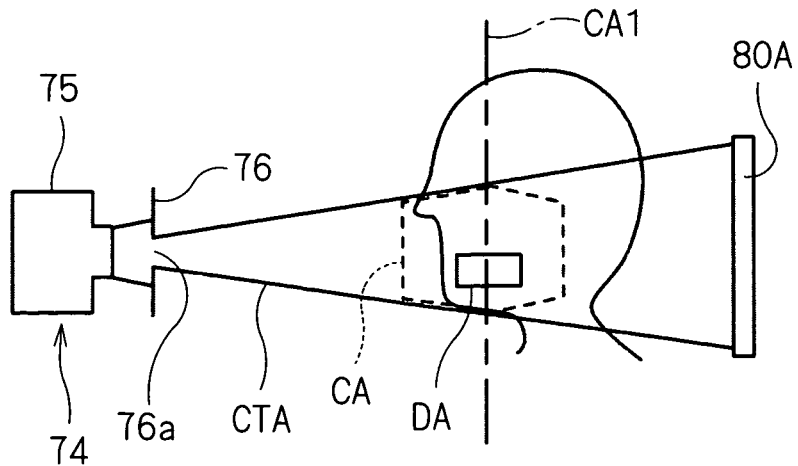
FIG. 15 is an illustration of a state of movement in performing the CT of the large radiation field.

FIGS. 14 and 15 are illustrations of a state of movement in performing the x-ray CT of the large radiation field. As shown in FIGS. 13, 14 and 15, in performing the x-ray CT of the large radiation field (the x-ray CT imaging mode for large radiation field), an operator inserts the cassette 82A for the x-ray CT of the large radiation field into the cassette holder 72a. In response to this, the opening 76a for the x-ray CT of the large radiation field is positioned to the front of the x-ray generator body 75 in the radiation direction. Then, an x-ray cone beam CTA for the x-ray CT of the large radiation field is emitted to an object such as a whole row of teeth DA and its transmission x-ray is detected by the x-ray image sensor 80A of the cassette 82A. In this state, the cassette 82A and the x-ray generator 74 are rotated about the central axis CA1 of a virtual space CA of substantial cylinder containing the whole row of teeth DA. This allows x-ray projection transmission data to be acquired from a plurality of directions around the row of teeth DA. The control part 110 described later performs image reconstruction and the like on the basis of the x-ray projection transmission data, to thereby obtain an x-ray CT image of the large radiation field on the row of teeth DA.

Further, by extracting data for generating a panoramic image form the x-ray projection transmission data for generating the x-ray CT image of the large radiation field, a panoramic tomography image can be also generated.

Figure 16:
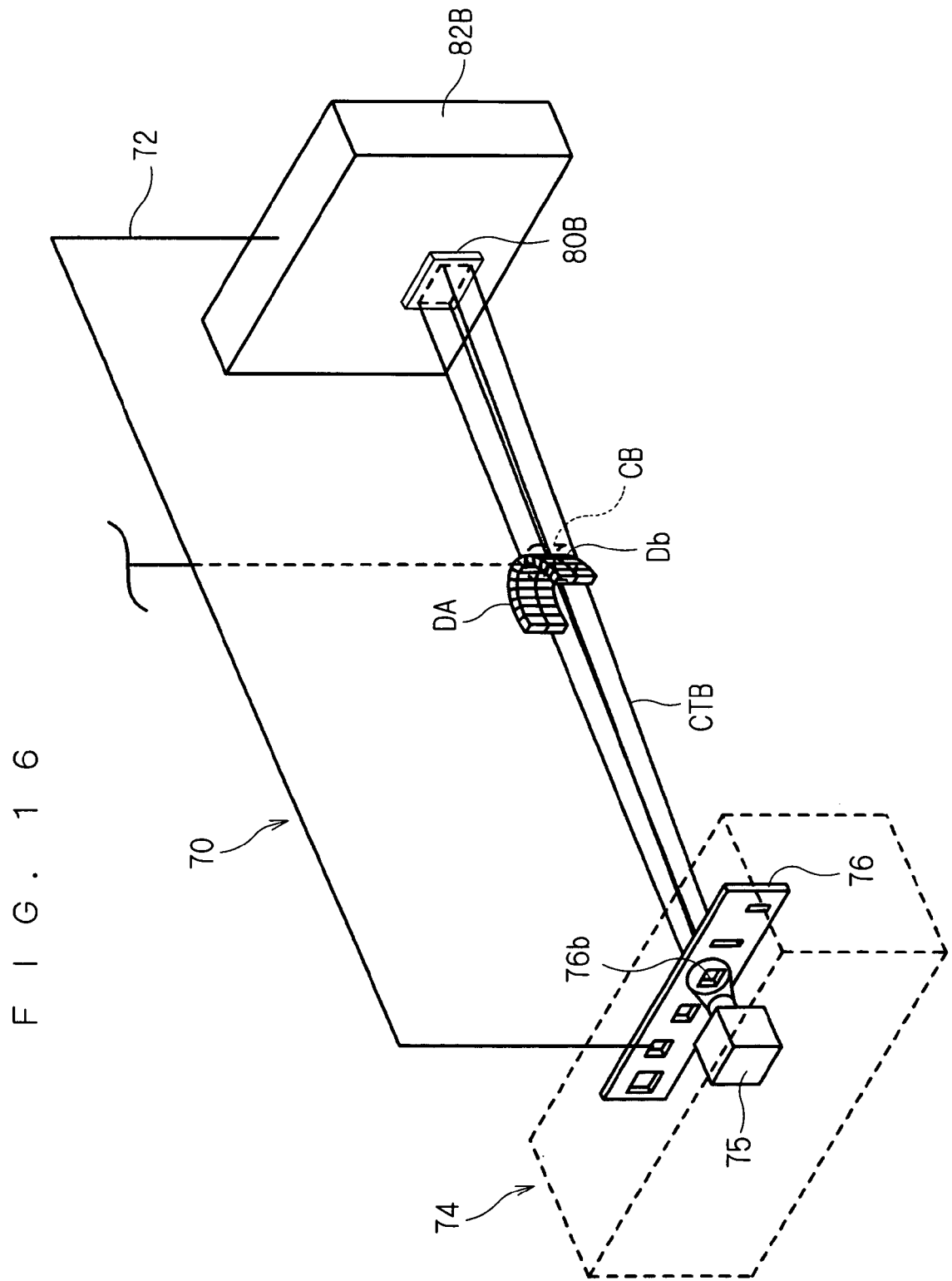
FIG. 16 is an illustration of a state where x-ray CT of the small radiation field is performed.
Figure 17:
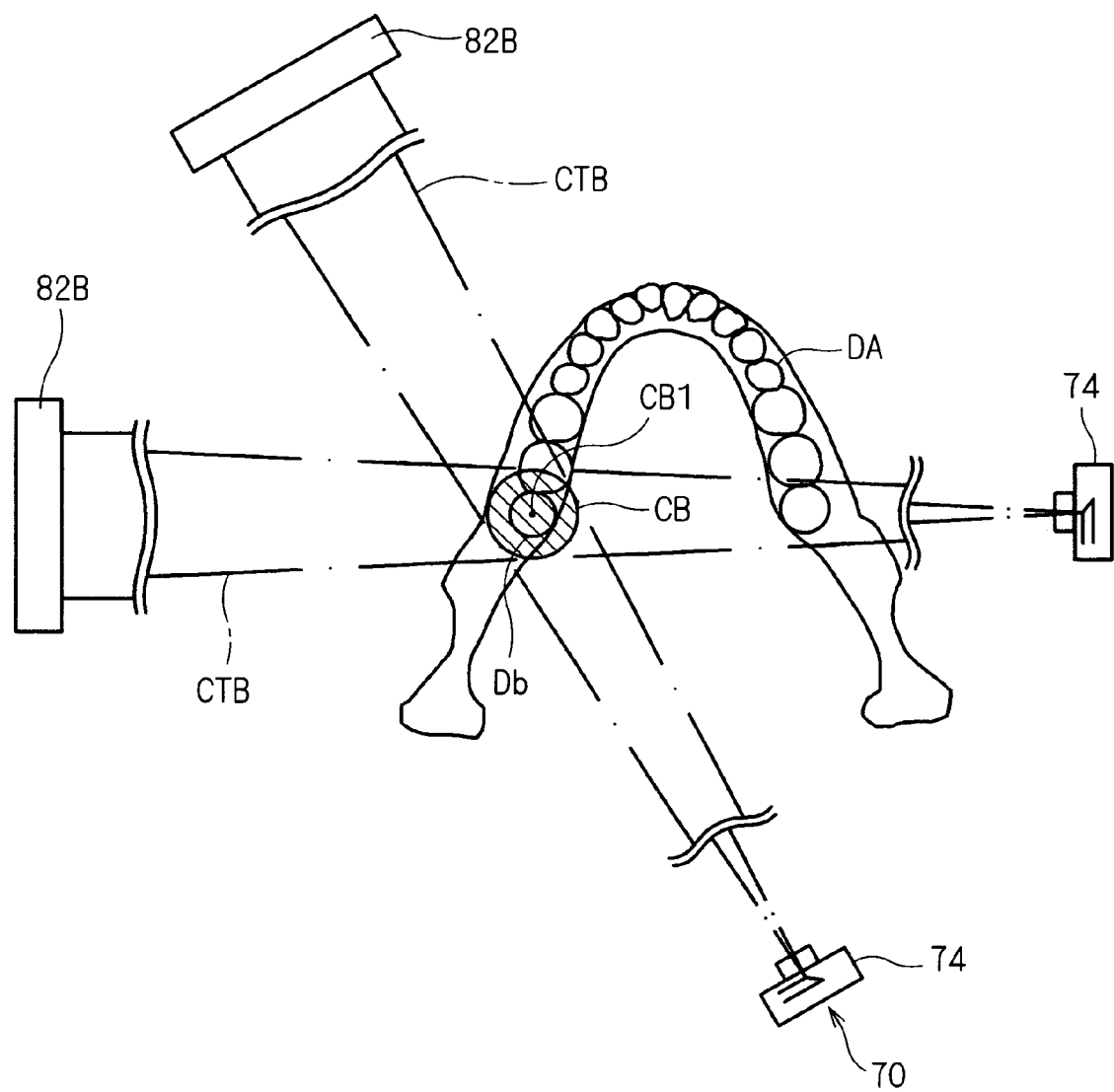
FIG. 17 is an illustration of a state of movement in performing the x-ray CT of the small radiation field.

FIG. 16 is an illustration of a state where the x-ray CT of the small radiation field is performed, and FIG. 17 is an illustration of a state of movement in performing the x-ray CT of the small radiation field.

In performing the x-ray CT of the small radiation field (in the x-ray CT imaging mode for small radiation field), the operator inserts the cassette 82B for the x-ray CT of the small radiation field into the cassette holder 72a. In response to this, the opening 76b for the x-ray CT of the small radiation field is positioned to the front of the x-ray generator body 75 in the radiation direction.

In the state of FIG. 16, used is the one of the three openings 73b, which is located almost midway between the opening 76b located at the highest position and the opening 76b located at the lowest position. Then, an x-ray cone beam CTB for the x-ray CT of the small radiation field is emitted to an object, such as a specified tooth Db, and its transmission x-ray is detected by the x-ray image sensor 80B of the cassette 82B. In this state, the cassette 82B and the x-ray generator 74 are rotated about the central axis CB1 of a virtual space CB of substantial cylinder containing the specified tooth Db. This allows x-ray projection transmission data to be acquired from a plurality of directions around the specified tooth Db. The control part 110 described later performs three-dimensional conversion and the like on the basis of the x-ray projection transmission data, to thereby obtain an x-ray CT image of the small radiation field on the specified tooth Db.

In performing the x-ray CT of the medium radiation field (in the x-ray CT imaging mode for medium radiation field), the operator inserts the cassette 82C for the x-ray CT of the small radiation field into the cassette holder 72*a*. In response to this, the opening 76*c* for the x-ray CT of the medium radiation field is positioned to the front of the x-ray generator body 75 in the radiation direction. In this state, in the same manner as in the above cases, an x-ray CT image of the medium radiation field on an object such as a plurality of teeth can be obtained. Since this case is the same as those cases of FIGS. 13 and 16 except use of the opening 76*c*, illustration thereof is omitted.

Figure 18:
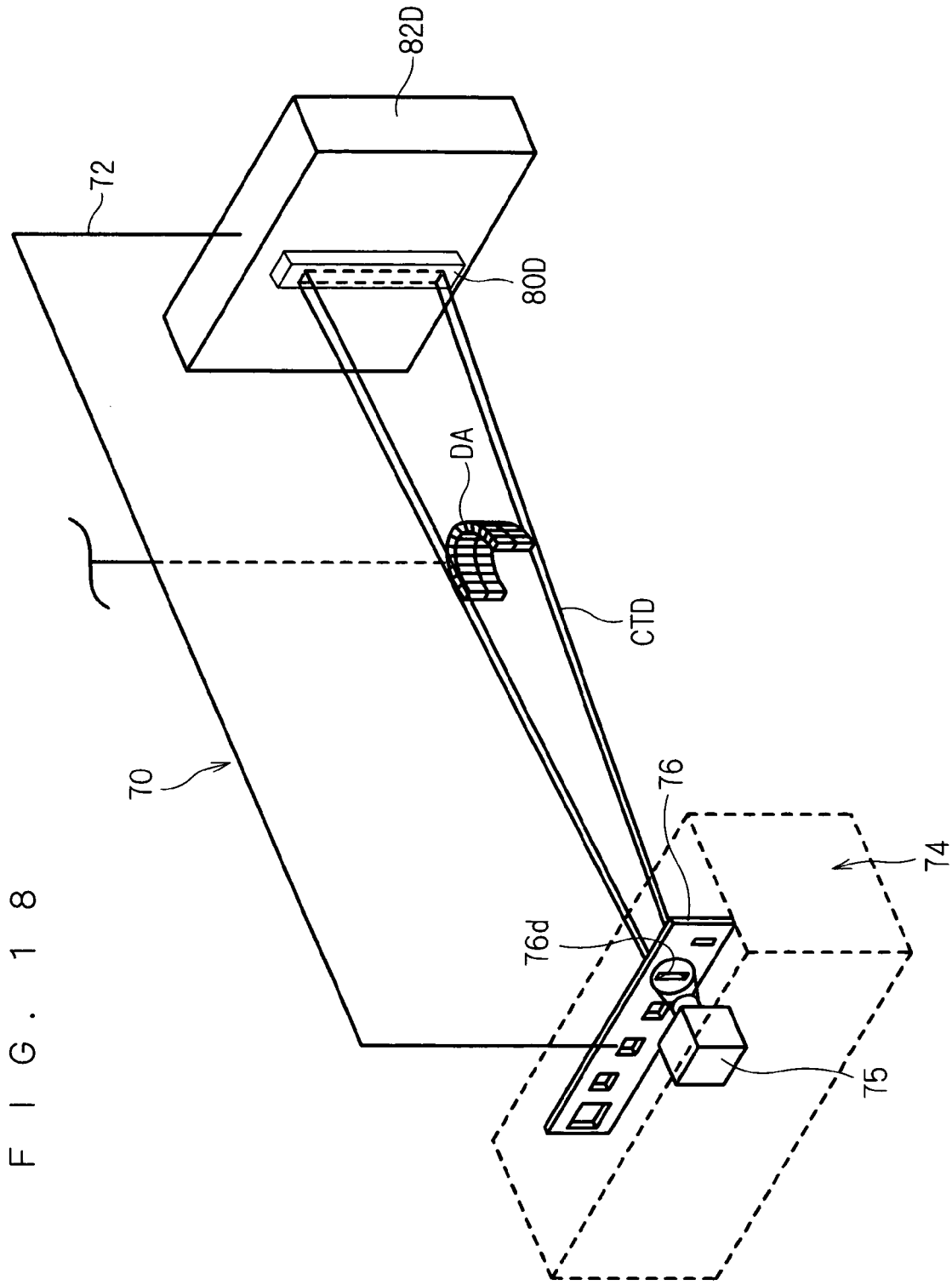
FIG. 18 is an illustration of a state where panoramic radiography is performed.

FIG. 18 is an illustration of a sate where the panoramic radiography is performed. In performing the panoramic radiography (in the panoramic imaging mode), the operator inserts the cassette 82D for the panoramic radiography into the cassette holder 72*a*. In response to this, the opening 76*d* for the panoramic radiography is positioned to the front of the x-ray generator body 75 in the radiation direction. Then, an x-ray slit beam CTD for the panoramic radiography is emitted to an object such as a row of teeth DA and its transmission x-ray is detected by the x-ray image sensor 80D of the cassette 82D. In this state, the row of teeth DA is scanned with the x-ray slit beam CTD while a rotation axis is so moved as to make the radiation direction of the x-ray slit beam CTD substantially orthogonal to an extension direction of the row of teeth DA, to thereby obtain an panoramic x-ray image through x-ray transmission radiography of the whole row of teeth DA along the dental arch.

<Block Configuration>

Figure 19:
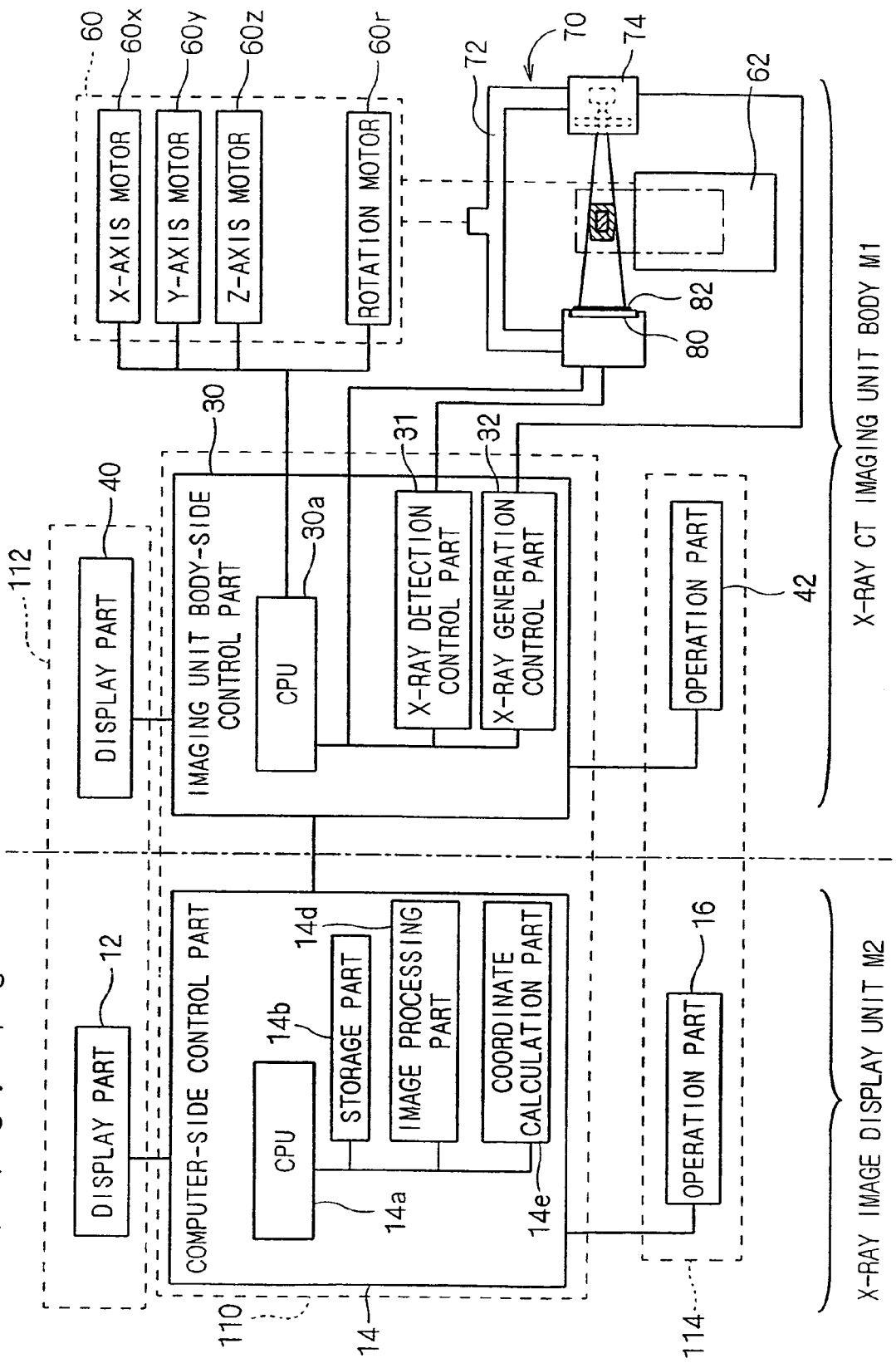
FIG. 19 is a block diagram showing the x-ray CT imaging apparatus.

FIG. 19 is a block diagram showing the x-ray CT imaging apparatus. This x-ray CT imaging apparatus comprises the x-ray CT imaging unit body M1 and the x-ray image display unit M2 as discussed above.

The x-ray CT imaging unit body M1 comprises the imaging unit body-side control part 30, the display part 40, the operation part 42, the moving mechanism part 60 and the imaging unit body 70.

The imaging unit body-side control part 30 is formed of a general-type computer having a CPU 30*a*, a ROM, a RAM and the like and performs predetermined processing in accordance with a software program stored in advance. Further, the imaging unit body-side control part 30 receives an operation command from the operator through the operation part 42 and displays information on the operation, a radiography result and the like on the display part 40.

This imaging unit body-side control part 30 has functions as an x-ray detection control part 31 and an x-ray generation control part. The x-ray generation control part 32 controls the x-ray generator 74, e.g., to set a radiation range of x-rays while moving the shield member 76 in accordance with the selected imaging mode, to set the amount of x-rays to be emitted, or the like. The x-ray detection control part 31 performs a control on the x-ray image sensor 80, such as an on-off control on the x-ray image sensor 80 or the like.

As discussed above, as the imaging modes, there are the x-ray CT imaging mode for large radiation field, the x-ray CT imaging mode for small radiation field, the x-ray CT imaging mode for medium radiation field, the panoramic imaging mode and the like. The respective x-ray CT imaging regions in the x-ray CT imaging mode for large radiation field, the x-ray CT imaging mode for small radiation field and the x-ray CT imaging mode for medium radiation field have different shapes. Herein, a different shape also includes a shape of the same contour and different size. For example, in the present invention, the case where the x-ray CT imaging regions in the x-ray CT imaging mode for large radiation field, the x-ray CT imaging mode for small radiation field and the x-ray CT imaging mode for medium radiation field have different shapes includes a case where the regions have similar contours and different volumes. As a matter of course, the case where the regions have different shapes includes a case where the regions have the same area and different contours. The x-ray CT in the x-ray CT imaging mode for large radiation field, the x-ray CT imaging mode for small radiation field and the x-ray CT imaging mode for medium radiation field may be local x-ray CT which is the x-ray CT on part of an object.

Selection of the imaging mode is performed in the following two manners. The mode to be selected includes a plurality of x-ray CT imaging modes such as the x-ray CT imaging mode for large radiation field, the x-ray CT imaging mode for small radiation field, the x-ray CT imaging mode for medium radiation field and the like.

In the first manner, the mode selection is performed by interchanging the cassette 82. Specifically, when one of the cassettes 82A, 82B, 82C and 82D is inserted into the cassette holder 72*a*, the inserted cassette 82A, 82B, 82C or 82D outputs type identifying information on its own type to the control part 110. The type identifying information is also an imaging mode signal for one of imaging modes including a plurality of x-ray CT imaging modes, and the control part 110 selects one of a plurality of imaging modes including a plurality of x-ray CT imaging modes on the basis of the type identifying information.

In the second manner, the mode selection is performed on the basis of an operation command received through an operation part 114 including the operation part 42 and the operation part 16. Specifically, the operation part 114 including the operation part 42 and the operation part 16 has a configuration to receive a setting command for the imaging mode and serves as an imaging mode selection part. The function of the imaging mode selection part may be given to both the operation part 42 and the operation part 16 to allow imaging mode selection through either the operation part 42 or the operation part 16, or may be given to one of the operation part 42 and the operation part 16. There may be a case where all the functions of the operation part 114 are given to one of the operation part 42 and the operation part 16 and the other is omitted.

The manner of inputting the setting command to the operation part 114 may be manipulation of any of switches corresponding to the imaging modes, use of switches or a touch panel while watching a selection screen displayed on a display part 112 including the display part 40 and the display part 12 or use of a keyboard or the like to directly input the imaging mode. Then, the control part 110 receives the setting command to select one of a plurality of imaging modes including a plurality of x-ray CT imaging modes.

Specifying information on the imaging mode selected by the operation part 114 is used for an operation for changing an imaging object region display discussed later and also used for various operations including an actual imaging operation in the x-ray CT imaging apparatus and the like, such as setting of the range of radiation field, setting of the amount of x-rays to be emitted, setting of the orbit of the x-ray generator 74 and the x-ray image sensor 80, display control of the display part 112 in accordance with the mode, and the like.

The functions as the x-ray detection control part 31 and the x-ray generation control part 32 may be those included in the processing performed by the computer including the above CPU 30a and the like or may be implemented by hardware provided separately from the computer. FIG. 19 shows that the functions as the x-ray detection control part 31 and the x-ray generation control part 32 are included in the imaging unit body-side control part 30.

Further, the imaging unit body-side control part 30 controls the X-axis motor 60x, the Y-axis motor 60y, the Z-axis motor 60z and the rotation motor 60r included in the moving mechanism part 60 in accordance with the selected imaging mode, the position of the imaging object which is set as discussed later and the like, to control the movement of the imaging unit body 70 so that imaging data of a desired object in a desired imaging mode can be obtained. Though FIG. 19 shows only one X-axis motor 60x, one Y-axis motor 60y, one Z-axis motor 60z and one rotation motor 60r, there may be a configuration where a plurality of X-axis motors 60x, Y-axis motors 60y, Z-axis motors 60z and rotation motors 60r are provided separately for the part of the moving mechanism part 60 on the side of the imaging unit body and for the part of the moving mechanism part 60 on the side of the holding part. The Z moving mechanism part and the Z-axis motor 60z have only to be provided in either the part of the moving mechanism part 60 on the side of the imaging unit body or the part of the moving mechanism part 60 on the side of the holding part but may be provided in both these parts. Further, only if positioning of the object in the Z-axis direction is correctly performed, the Z moving mechanism part and the Z-axis motor 60z may be omitted in both the part of the moving mechanism part 60 on the side of the imaging unit body and the part of the moving mechanism part 60 on the side of the holding part.

The imaging unit body-side control part 30 is connected intercommunicably to the computer-side control part 14 and gives information including the x-ray projection data outputted from the x-ray image sensor 80 to the computer-side control part 14.

The x-ray image display unit M2 has the display part 12 such as a liquid crystal display (LCD) and the like, the computer-side control part 14 and the operation part 16 such as a keyboard, a mouse and the like. The operation part 16 receives the operation command and gives it to the computer-side control part 14. The display part 12 displays a predetermined information on the basis of an image output signal from the computer-side control part 14. An image displayed on the display part 12 is information on the operation, information on the radiography result or the like.

The computer-side control part 14 is formed of a general computer having a CPU 14a, a ROM and a RAM and also having a storage part 14b such as a hard disk device or the like and performs predetermined processing in accordance with a software program stored in advance.

The computer-side control part 14 has functions as an image processing part 14d and a coordinate calculation part 14e.

The coordinate calculation part 14e performs an operation for converting two-dimensional data into three-dimensional data on the basis of the x-ray projection data outputted from the x-ray image sensor 80, to generate CT image data. Further, the coordinate calculation part 14e converts the position of the imaging object specified by the display part 112 (imaging object region display) as discussed later into coordinate data in accordance with the actual position of the imaging object, to generate position data so that the imaging unit body 70 can be moved to an appropriate imaging position with respect to the object in accordance with the imaging mode and output the position data to the imaging unit body-side control part 30. On the basis of the position data, the imaging unit body-side control part 30 performs a movement control on the imaging unit body 70.

The image processing part 14d generates an image to be displayed on the display part 12. The image to be generated includes, e.g., an image for operation, a position setting image, an x-ray image indicating the radiography result and the like.

The coordinate calculation part 14e and the image processing part 14d serve as an image generation part which is capable of generating an x-ray image (including an x-ray CT image) in accordance with the imaging mode (including the x-ray CT imaging mode) selected on the basis of the x-ray projection data outputted from the x-ray image sensor 80 and capable of generating an image obtained by superposing the imaging object region display on the position setting image representing the object. The latter function and operation will be discussed next in detail.

The respective functions as the coordinate calculation part 14e and the image processing part 14d, however, may be included in the processing performed by the above CPU 14a and the like or may be implemented by hardware provided separately from the CPU and the like. FIG. 19 shows that these functions are included in the function of the computer-side control part 14.

The storage part 14b stores respective imaging object region display images for various imaging modes, being brought into correspondence with the imaging modes. Each imaging object region display image represents an imaging region in accordance with the imaging mode. Herein, since position setting is performed on the basis of a dental arch image schematically representing a dental arch and a panoramic x-ray image, the imaging object region display images are stored in correspondence with the types of position setting screens. Specific examples thereof will be discussed later. As a matter of course, the data obtained by bringing the imaging object region display images into correspondence with the imaging modes do not need to be stored in the storage part 14b but have only to be stored in a device accessible to the control part 110.

The computer-side control part 14 and the imaging unit body-side control part 30 are intercommunicable with each other and included in the control part 110 which, as a whole, controls the x-ray CT imaging apparatus, and each of the functions of the computer-side control part 14 and the imaging unit body-side control part 30 may be performed by any one of these. Further, there may be a case where one of the computer-side control part 14 and the imaging unit body-side control part 30 is omitted and all the functions are performed by the other. There may be another case where another computer is further connected intercommunicably to these parts and three or more control parts perform the processings in cooperation.

The operation part 16 and the operation part 42 are included in the operation part 114 which, as a whole, receives a command for the x-ray CT imaging apparatus, and the display part 12 and the display part 40 are included in the display part 112 which, as a whole, displays various information on the x-ray CT imaging apparatus. The operation commands discussed above or later may be given to any one of the operation part 16 and the operation part 42. Further, the display details discussed above or later may be displayed on any one of the display part 12 and the display part 40.

<Setting Screen for Imaging Object Region>

Exemplary setting screens for setting the imaging object regions will be discussed. As the setting screens, there are two types, one type in which the dental arch which is an imaging object is schematically shown, not based on its real image and the other type in which an actual radiography image of the dental arch is displayed.

Figure 20:
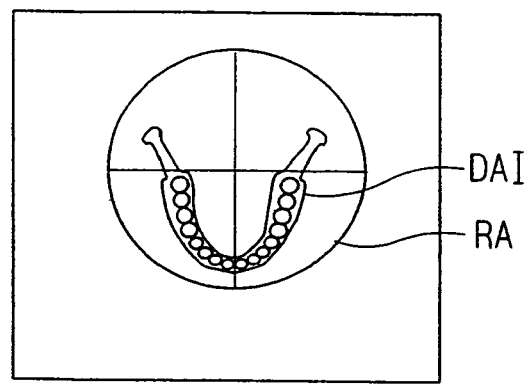
FIG. 20 is a view showing an exemplary position setting screen used for radiography in the x-ray CT imaging mode for large radiation field.

First, the former type will be discussed. In FIG. 20, a dental arch image DAI schematically representing a dental arch is displayed as a position setting image. This dental arch image DAI represents a dental arch of a general adult and is stored in the storage part 14b of the control part 110 in advance. Further, there may be a case where different dental arches for children and adults are stored and a dental arch in accordance with an object person is specified and displayed.

An imaging object region display RA in accordance with the x-ray CT imaging mode for large radiation field to be superposed on this dental arch image DAI is stored in the storage part 14b in advance. The x-ray CT imaging mode for large radiation field is a mode where the CT is performed on a whole row of teeth and therefore the imaging object region display RA in accordance with the x-ray CT imaging mode for large radiation field is set to have an enough size to contain the whole of the above dental arch image DAI. Herein, the imaging object region display RA is a circular line which can contain the whole of the dental arch image DAI, including its center and cross-like lines indicating orthogonal coordinate axes.

When the x-ray CT imaging mode for large radiation field is selected, the image processing part 14d determines the imaging object region display RA in accordance with the x-ray CT imaging mode for large radiation field and generates an image by superposing the imaging object region display RA on the above dental arch image DAI to display it on the display part 112.

Figure 21:
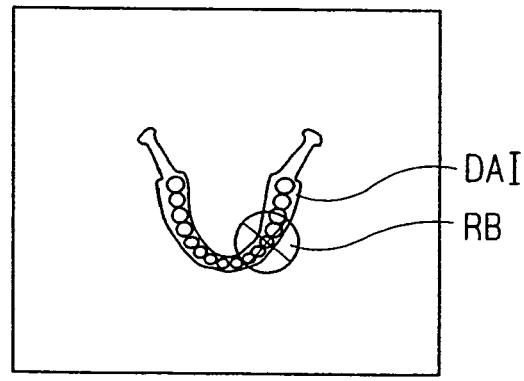
FIG. 21 is a view showing an exemplary position setting screen used for radiography in the local x-ray CT imaging mode for small radiation field.

FIG. 21 shows a position setting screen used for the radiography in the x-ray CT imaging mode for small radiation field. In this case, an imaging object region display RB in accordance with the x-ray CT imaging mode for small radiation field is stored in the storage part 14b in advance. The x-ray CT imaging mode for small radiation field is a mode where the CT is performed on specified teeth and therefore the imaging object region display RB in accordance with this mode is set to have an enough size to contain the specified teeth. Herein, the imaging object region display RB is a circular line which can contain the specified teeth (herein, about three to five teeth) in the above dental arch image DAI, including its center and cross-like lines indicating orthogonal coordinate axes.

When the x-ray CT imaging mode for small radiation field is selected, the image processing part 14d determines the imaging object region display RB in accordance with this mode and generates an image by superposing the imaging object region display RB on the above dental arch image DAI to display it on the display part 112. Further, in this state, in response to the command from the operation part 114, the imaging object region display RB can be moved relatively to the dental arch image DAI. As the commands from the operation part 114, there are a command given by using a touch pen, a command given by using direction keys and the like. Then, in a state where the imaging object region display RB has been moved to a desired position with respect to the dental arch image DAI, when a position determining command is inputted through the operation part 114, an imaging range in the x-ray CT imaging mode for small radiation field can be specified.

Figure 22:
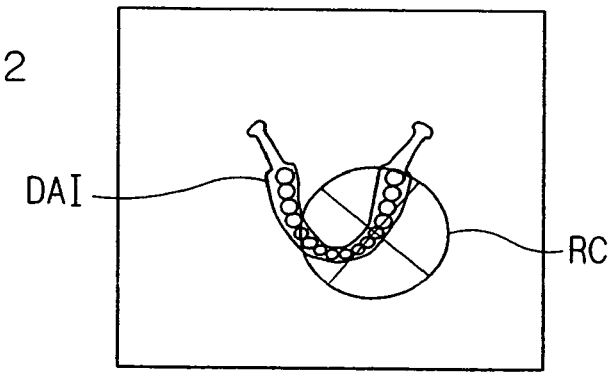
FIG. 22 is a view showing an exemplary position setting screen used for radiography in the local x-ray CT imaging mode for medium radiation field.

FIG. 22 shows a position setting screen used for the radiography in the x-ray CT imaging mode for medium radiation field. In this case, an imaging object region display RC in accordance with the x-ray CT imaging mode for medium radiation field is stored in the storage part 14b in advance. The x-ray CT imaging mode for medium radiation field is a mode where the CT is performed on more teeth than those in the above x-ray CT imaging mode for small radiation field and therefore the imaging object region display RC in accordance with this mode is set smaller than the imaging object region display RA and larger than the imaging object region display RB. Herein, the imaging object region display RC is a circular line which can contain specified teeth which correspond to about a third to a half of the dental arch image DAI, including its center and cross-like lines indicating orthogonal coordinate axes.

When the x-ray CT imaging mode for medium radiation field is selected, the image processing part 14d determines the imaging object region display RC in accordance with this mode and generates an image by superposing the imaging object region display RC on the above dental arch image DAI to display it on the display part 112. Further, in this state, in response to the command from the operation part 114, the imaging object region display RC can be moved relatively to the dental arch image DAI. Then, in a state where the imaging object region display RC has been moved to a desired position with respect to the dental arch image DAI, when the position determining command is inputted through the operation part 114, an imaging range in the x-ray CT imaging mode for medium radiation field can be specified.

When the position of the imaging object region display RB or RC is set with respect to the dental arch image DAI, as discussed above, in the range specified thus, for the x-ray CT of the small radiation field or the medium radiation field, the operations in accordance with the selected mode and position, such as determination of the orbit of the x-ray generator 74 and the x-ray image sensor 80 and the like, are performed.

Figure 23:
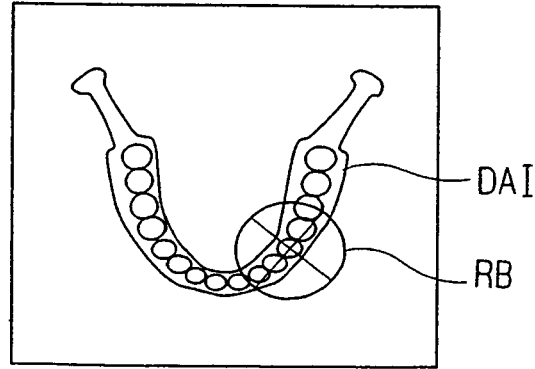
FIG. 23 is a view showing another exemplary position setting screen used for radiography in the local x-ray CT imaging mode for small radiation field.

In these modes, though the dental arch image DAI may be always displayed in the same size, the dental arch image DAI does not always need to be displayed in the same size, and as shown in FIG. 23, for example, the dental arch image DAI may be displayed, being enlarged, in the x-ray CT imaging mode for small radiation field. In this case, of course, the imaging object region display RB is displayed, being enlarged, in accordance with the enlargement ratio of the dental arch image DAI. Further, the dental arch image DAI which is the position setting image may be displayed, being reduced or enlarged, while the size and the like of the imaging object region display displayed on the display part 112 is kept substantially constant. There may be a case, for example, where the sizes of the respective displayed circles of the imaging object region display RA of FIG. 20, the imaging object region display RB of FIG. 21 and the imaging object region display RC of FIG. 22 are set the same and the size of the displayed dental arch image DAI is changed depending on the mode.

In the present invention, moving the imaging object region display relatively to the position setting image such as the dental arch image DAI by the operation part refers to moving the imaging object region display by the operation part while keeping the position setting image still, moving the position setting image by the operation part while keeping the imaging object region display still and moving the position setting image and the imaging object region display simultaneously or alternately by the operation part.

Since each of the imaging object region displays RA, RB and RC has only to be moved relatively to the dental arch image DAI, each of the imaging object region displays RA, RB and RC may be moved on the fixed dental arch image DAI or the dental arch image DAI may be moved on each of the fixed imaging object region displays RA, RB and RC. Further, both the dental arch image DAI and each of the imaging object region displays RA, RB and RC may be moved independently from each other.

The latter type in which a radiography image of the row of teeth is displayed as the setting screen for setting the imaging object region will be herein discussed. FIG. 24 shows a panoramic x-ray image obtained by actually performing radiography of the row of teeth. In other words, for this type of position setting, an image representing the whole row of teeth needs to be obtained in advance. Herein, discussion will be made on an exemplary case where a panoramic x-ray image or the like of the whole row of teeth is obtained in advance. In FIG. 24, as the position setting image displayed is an image XP obtained by performing panoramic radiography of the whole row of teeth from the front in advance. This image XP is also called a scout view image when it is used for position setting.

When radiography is performed in the x-ray CT imaging mode for large radiation field, an imaging object region display CSA in accordance with this mode is stored in the storage part 14*b* in advance. The imaging object region display CSA in accordance with the x-ray CT imaging mode for large radiation field is set to have an enough size to contain the whole row of teeth in the panoramic x-ray image XP. Herein, the imaging object region display CSA is a substantially quadrate line which can contain the whole row of teeth, including its center and cross-like lines indicating orthogonal coordinate axes.

When the x-ray CT imaging mode for large radiation field is selected, the image processing part 14*d* determines the imaging object region display CSA in accordance with the x-ray CT imaging mode for large radiation field and generates an image by superposing the imaging object region display CSA on the above panoramic x-ray image XP to display it on the display part 112.

In the x-ray CT imaging mode for large radiation field, since the imaging object region display CSA is set to have an enough size to contain the whole row of teeth, the position of the imaging object region display CSA do not usually need to be changed. An actual position of the row of teeth, however, can deviate from a position which is originally supposed. For this reason, the position of the imaging object region display CSA may be set movable with respect to the above panoramic x-ray image XP, to perform the x-ray CT of the large radiation field in accordance with the specified position.

FIG. 25 shows a position setting screen used for radiography in the x-ray CT imaging mode for small radiation field. In this case, an imaging object region display CSB in accordance with the x-ray CT imaging mode for small radiation field is stored in the storage part 14*b* in advance. The imaging object region display CSB in accordance with the x-ray CT imaging mode for small radiation field is set to have an enough size to contain specified teeth. Herein, the imaging object region display CSB is a substantially quadrate line which can contain the specified teeth (herein, about three to five teeth) in the above panoramic x-ray image XP, including its center and cross-like lines indicating orthogonal coordinate axes.

When the x-ray CT imaging mode for small radiation field is selected, the image processing part 14*d* determines the imaging object region display CSB in accordance with this mode and generates an image by superposing the imaging object region display CSB on the above panoramic x-ray image XP to display it on the display part 112. Further, in this state, in response to the command from the operation part 114, the imaging object region display CSB can be moved relatively to the panoramic x-ray image XP. Then, in a state where the imaging object region display CSB has been moved to a desired position with respect to the panoramic x-ray image XP, when the position determining command is inputted through the operation part 114, an imaging range in the x-ray. CT imaging mode for small radiation field can be specified.

FIG. 26 shows a position setting screen used for radiography in the x-ray CT imaging mode for medium radiation field. In this case, an imaging object region display CSC in accordance with the x-ray CT imaging mode for medium radiation field is stored in the storage part 14*b* in advance. The imaging object region display CSC in accordance with the x-ray CT imaging mode for medium radiation field is set smaller than the imaging object region display CSA and larger than the imaging object region display CSB. Herein, the imaging object region display CSC is a substantially quadrate line which can contain specified teeth which correspond to about a third to a half of the above row of teeth, including its center and cross-like lines indicating orthogonal coordinate axes.

When the x-ray CT imaging mode for medium radiation field is selected, the image processing part 14*d* determines the imaging object region display CSC in accordance with this mode and generates an image by superposing the imaging object region display CSC on the above panoramic x-ray image XP to display it on the display part 112. Further, in this state, in response to the command from the operation part 114, the imaging object region display CSC can be moved relatively to the panoramic x-ray image XP. Then, in a state where the imaging object region display CSB has been moved to a desired position with respect to the panoramic x-ray image XP, when the position determining command is inputted through the operation part 114, an imaging range in the x-ray CT imaging mode for medium radiation field can be specified.

When the position of the imaging object region display CSA, CSB or CSC is set with respect to the panoramic x-ray image XP as discussed above, in the range specified thus, for the x-ray CT of the large radiation field, the small radiation field or the medium radiation field, the operations in accordance with the selected mode and position, such as determination of the orbit of the x-ray generator 74 and the x-ray image sensor 80 and the like, are performed.

As a matter of course, in these cases, the panoramic x-ray image XP and the imaging object region displays CSA, CSB and CSC may be displayed, being reduced or enlarged.

Since each of the imaging object region displays CSA, CSB and CSC has only to be moved relatively to the panoramic x-ray image XP, each of the imaging object region displays CSA, CSB and CSC may be moved on the fixed panoramic x-ray image XP or the panoramic x-ray image XP may be moved on each of the fixed imaging object region displays CSA, CSB and CSC. Further, both the panoramic x-ray image XP and each of the imaging object region displays CSA, CSB and CSC may be moved.

Further, the above display may be performed by any one of the display parts 12 and 40 and the operations may be received by any one of the operation parts 16 and 42.

The type in which the actual radiography image of the row of teeth is displayed as the setting screen is not limited to the exemplary case of using the panoramic x-ray image. If the CT is performed in the above-discussed x-ray CT imaging mode for large radiation field in advance and a tomography image in which the dental arch is viewed in plane from the top of the head is obtained, for example, the tomography image can be used as the position setting image. In other words, the tomography image in which the dental arch is viewed in plane can be used as the position setting image which is a real image version of the dental arch image DAI schematically representing the dental arch shown in FIGS. 20 to 23.

The tomography image is not limited to one in which the dental arch is viewed in plane from the top of the head, but a tomography image viewed from any direction may be used as appropriate.

Further, in a case where the CT is performed in the x-ray CT imaging mode for large radiation field or in the x-ray CT imaging mode for medium radiation field, a volume rendering image which is a stereoscopic 3D image representing a solid tissue of the object may be generated by image reconstruction, to be used as the position setting image, or a 3D image of stereoscopic horseshoe shape obtained by extracting a part which corresponds to panoramic tomography ma be used as the position setting image.

The type of position setting image in which the row of teeth is displayed by using the actual radiography image may be generated with its resolution set lower than those of the x-ray CT image and the panoramic x-ray image of the main radiography, for reduction in the load of operation.

<Operation>

Figure 27:
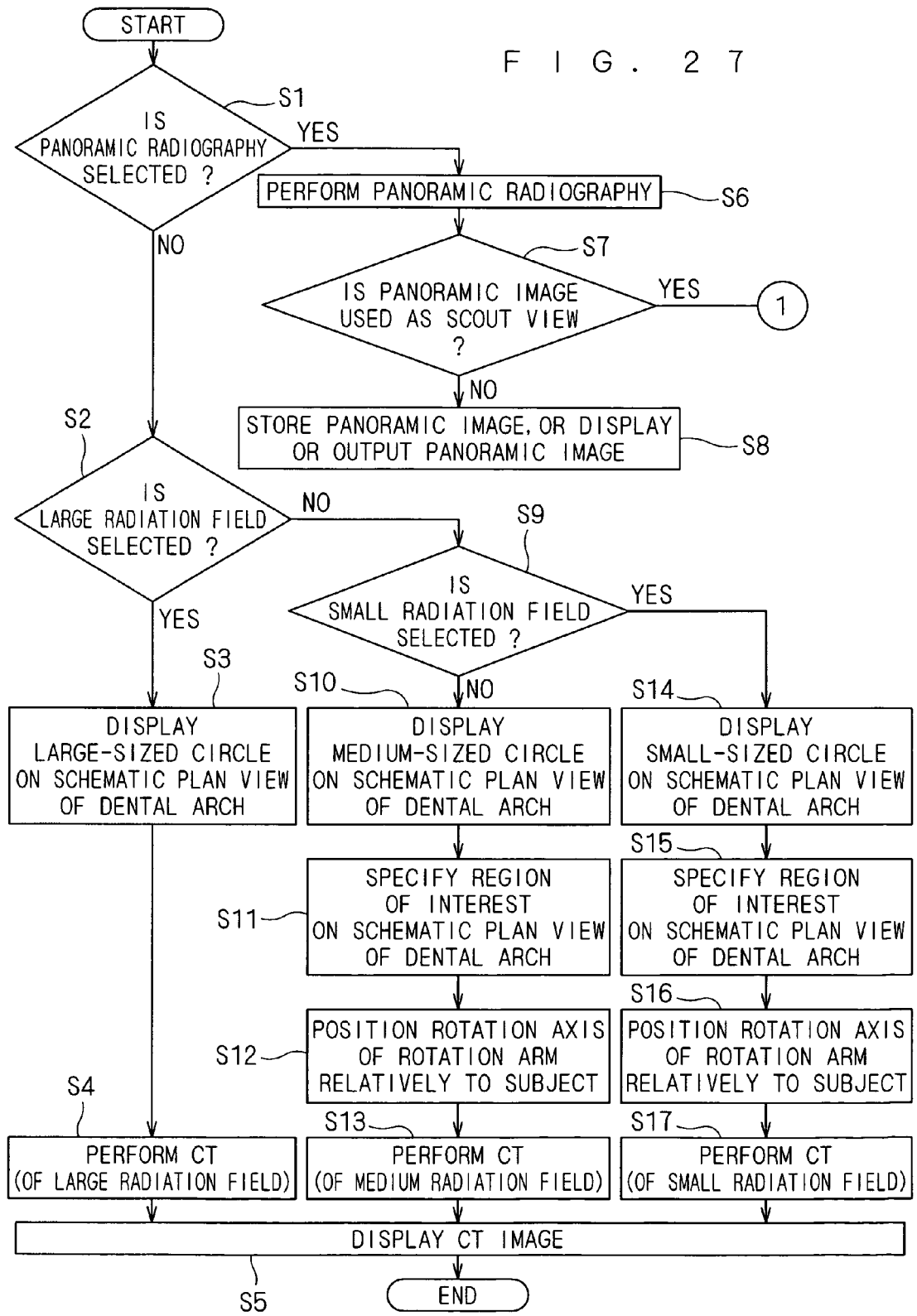
FIG. 27 is a flowchart showing an operation of the x-ray CT imaging apparatus.
Figure 28:
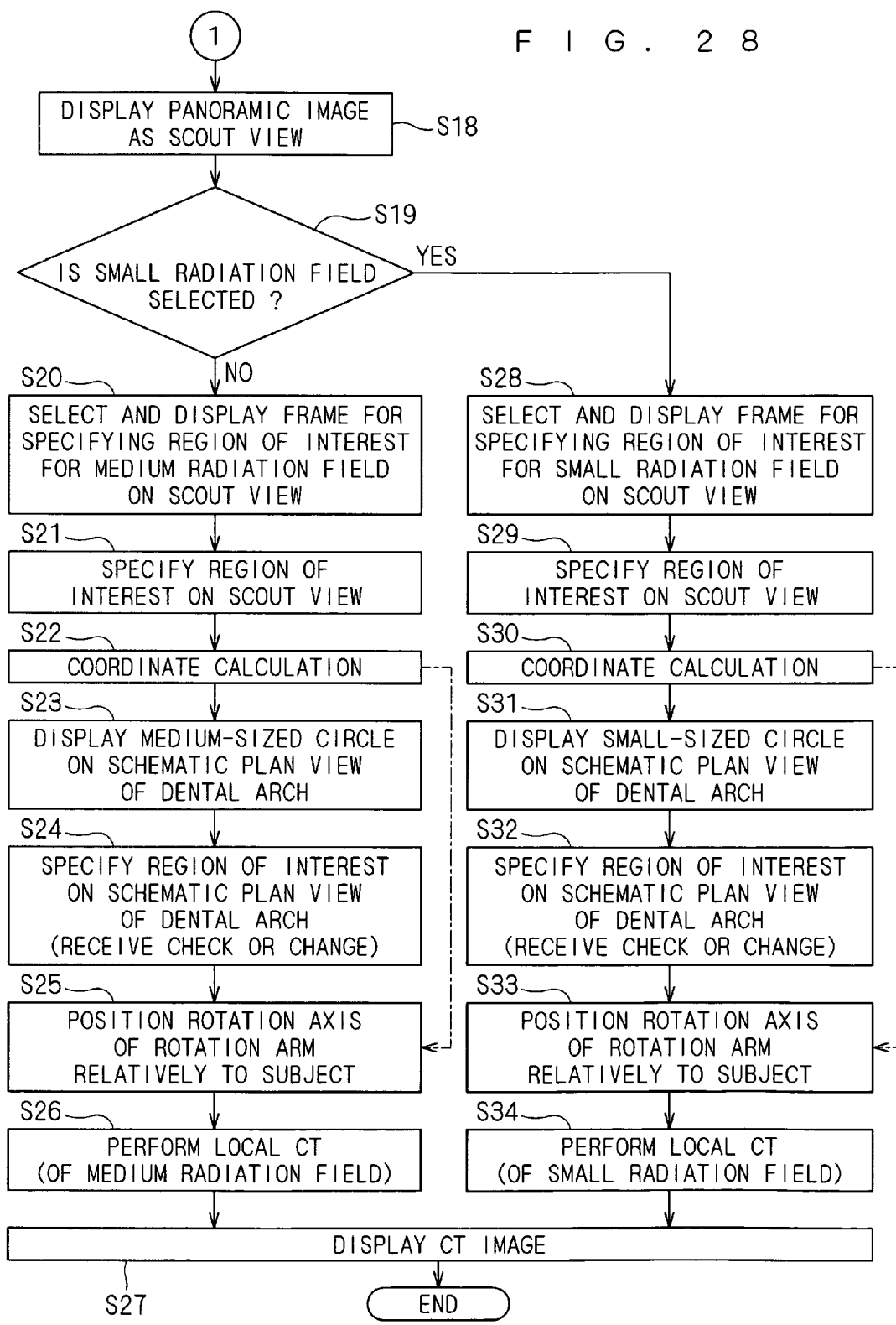
FIG. 28 is a flowchart showing an operation of the x-ray CT imaging apparatus.

An operation of the x-ray CT imaging apparatus will be discussed, particularly focusing attention on a position setting operation. FIGS. 27 and 28 are flowcharts showing the operation of the x-ray CT imaging apparatus.

First, in Step S1, whether the panoramic radiography is selected or not is determined. If it is judged that the panoramic radiography is not selected, on the basis of the setting command given to the operation part 114 or the type identifying information from the information processing part 83 of the inserted cassette 82, the process goes to Step S2.

In Step S2, whether the x-ray CT of the large radiation field is selected or not is determined. If it is judged that the x-ray CT of the large radiation field is selected, on the basis of the setting command given to the operation part 114 or the type identifying information from the information processing part 83 of the inserted cassette 82, the process goes to Step S3 (the x-ray CT imaging mode for large radiation field).

In Step S3, an image obtained by superposing the imaging object region display RA including a large-sized circle on the dental arch image DAI schematically representing a dental arch in plane is displayed on the display part 112 (see FIG. 20). Subsequently, going to Step S4, the x-ray CT of the large radiation field (radiography of the large radiation field) is performed. Next, going to Step S5, an x-ray CT image of the large radiation field which is obtained is displayed on the display part 112, and the process is finished.

In Step S2, if it is judged that the x-ray CT of the large radiation field is not selected, the process goes to Step S9. In Step S9, whether the small radiation field is selected or not, in other words, whether the x-ray CT imaging mode for small radiation field is selected or not is determined, on the basis of the setting command given to the operation part 114 or the type identifying information from the information processing part 83 of the inserted cassette 82. If it is judged that the small radiation field is not selected, the process goes to Step S10 (selection of the x-ray CT imaging mode for medium radiation field).

In Step S10, an image obtained by superposing the imaging object region display RC including a medium-sized circle on the dental arch image DAI schematically representing the dental arch in plane is displayed on the display part 112 (see FIG. 22). Subsequently, going to Step S11, the position setting command for the imaging object region display RC with respect to the dental arch image DAI is received through the operation part 114.

Next, in Step S12, the moving mechanism part 60 is driven in accordance with the position of the imaging object region display of Step S11, to position the rotation axis of the rotation arm 72 and the like relatively to the object. In this state, in next Step S13, the moving mechanism part 60, the x-ray generator 74 and the x-ray image sensor 80 are driven to perform the x-ray CT of the medium radiation field (radiography of the medium radiation field).

Next, going to Step S5, an x-ray CT image of the medium radiation field which is obtained is displayed on the display part 112, and the process is finished.

In Step S9, if it is judged that the small radiation field is selected, the process goes to Step S14 (selection of the x-ray CT imaging mode for small radiation field).

In Step S14, an image obtained by superposing the imaging object region display RB including a small-sized circle on the dental arch image DAI schematically representing the dental arch in plane is displayed on the display part 112 (see FIG. 21). Subsequently, going to Step S15, the position setting command for the imaging object region display RB with respect to the dental arch image DAI is received through the operation part 114.

Next, in Step S16, the moving mechanism part 60 is driven in accordance with the position of the imaging object region display of Step S15, to position the rotation axis of the rotation arm 72 and the like relatively to the object. Then, in next Step S17, the moving mechanism part 60, the x-ray generator 74 and the x-ray image sensor 80 are driven to perform the x-ray CT of the small radiation field (radiography of the small radiation field).

Next, going to Step S5, an x-ray CT image of the small radiation field which is obtained is displayed on the display part 112, and the process is finished.

In Step S1, if it is judged that the panoramic radiography is selected, the process goes to Step S6. Then, in Step S6, the panoramic radiography is performed. A panoramic x-ray image of the whole row of teeth is thereby obtained.

In next Step S7, whether the panoramic x-ray image is used as a scout view image or not is determined, on the basis of the command given to the operation part 114. If it is judged that the panoramic x-ray image is not used as the scout view image (if the process is finished only with radiography to obtain the panoramic x-ray image, or the like), the process goes to Step S8.

In Step S8, the above panoramic x-ray image is stored as data or an output operation, such as display of the panoramic x-ray image on the display part 112 or the like, is performed, and the process is finished.

In Step S7, if it is judged that the panoramic x-ray image is used as the scout view image, the process goes to Step S18. In Step S18, the panoramic x-ray image XP is displayed as the scout view image and the process goes to nest Step S19.

In Step S19, whether the small radiation field is selected or not is determined on the basis of the command given to the operation part 114 or the type identifying information from the information processing part 83 of the inserted cassette 82. If it is judged that the small radiation field is not selected, the process goes to Step S20 (selection of the x-ray CT imaging mode for medium radiation field).

In Step S20, an image obtained by superposing the imaging object region display CSC which is selected as a frame for specifying the imaging object region for medium radiation field on the panoramic x-ray image XP which is the above scout view image is displayed on the display part 112 (see FIG. 26), and the process goes to Step S21.

In Step S21, the position setting command for the imaging object region display CSC with respect to the panoramic x-ray image XP (panoramic view image) is received through the operation part 114. Then, in next Step S22, coordinate calculation is performed to obtain the position of the rotation axis of the rotation arm 72 and the like in accordance with the specified position from a relatively positional relation of the imaging object region display CSC with respect to the panoramic x-ray image XP (panoramic view image), and Steps S23 and S24 are executed. Steps S23 and S24 are the same operations as those in above Steps S10 and S11, and the position specified in Step S21 is displayed on the dental arch image DAI. These operations are performed to allow a check and the like, and as the result of the check, if the position needs to be changed, the instruction for change is received and a change operation is performed in Step S24, and if the position does not need to be changed, the process goes to Step S25. These Steps S23 and S24 may be omitted.

Then, the process goes to Step S25. In Step S25, the moving mechanism part 60 is driven in accordance with the position of the imaging object region display of Step S21 or S24, to position the rotation axis of the rotation arm 72 relatively to the object. After that, in next Step S26, the moving mechanism part 60, the x-ray generator 74 and the x-ray image sensor 80 are driven to perform the x-ray CT of the medium radiation field (radiography of the medium radiation field).

Next, going to Step S27, an x-ray CT image of the medium radiation field which is is obtained is displayed on the display part 112, and the process is finished.

In Step S19, if it is judged that the small radiation field is selected, the process goes to Step S28 (selection of the x-ray CT imaging mode for small radiation field).

In Step S28, an image obtained by superposing the imaging object region display CSB which is selected as a frame for specifying the imaging object region for small radiation field on the panoramic x-ray image XP which is the above scout view image is displayed on the display part 112 (see FIG. 25), and the process goes to Step S29.

In Step S29, the position setting command for the imaging object region display CSB with respect to the panoramic x-ray image XP (panoramic view image) is received through the operation part 114. Then, in next Step S30, coordinate calculation is performed to obtain the position of the rotation axis of the rotation arm 72 and the like in accordance with the specified position from a relatively positional relation of the imaging object region display CSC with respect to the panoramic x-ray image XP (panoramic view image), and Steps S31 and S32 are executed. Steps S31 and S32 are the same operations as those in above Steps S14 and S15, and the position specified in Step S29 is displayed on the dental arch image DAI. These operations are performed to allow a check and the like, and as the result of the check, if the position needs to be changed, the instruction for change is received and a change operation is performed in Step S32, and if the position does not need to be changed, the process goes to Step S33. These Steps S31 and S32 may be omitted.

Then, the process goes to Step S33. In Step S33, the moving mechanism part 60 is driven in accordance with the position of the imaging object region display of Step S29 or S32, to position the rotation axis of the rotation arm 72 relatively to the object. After that, in next Step S34, the moving mechanism part 60, the x-ray generator 74 and the x-ray image sensor 80 are driven to perform the x-ray CT of the small radiation field (radiography of the small radiation field).

Next, going to Step S27, an x-ray CT image of the small radiation field which is obtained is displayed on the display part 112, and the process is finished.

Steps S5 and S27 are the steps for generating the x-ray CT image in accordance with the selected x-ray CT imaging mode.

In the x-ray CT imaging apparatus having the above configuration, the image generation part including the coordinate calculation part 14*e* and the image processing part 14*d* changes the imaging object region display RA, RB, RC, CSA, CSB or CSC in accordance with the imaging mode selected on the basis of the inserted cassette 82 or the imaging mode selected on the basis of the operation command through the operation part 114. Therefore, conveniently, the imaging object region display RA, RB, RC, CSA, CSB or CSC used for positioning and the like can be easily changed in accordance with the imaging mode.

Especially, since the imaging object region display RA, RB, RC, CSA, CSB or CSC can be changed in accordance with the imaging mode selected on the basis of the interchange of the cassette 82 including the x-ray image sensor 80, it is a great convenience that the interchange of the cassette 82 automatically changes the imaging object region display RA, RB, RC, CSA, CSB or CSC.

Further, when the imaging object region display RA, RB, RC, CSA, CSB or CSC is changed in response to the setting command given to the operation part 114 by the operator, it is convenient that the imaging object region display RA, RB, RC, CSA, CSB or CSC can be changed in response to an individual command.

Figure 29:
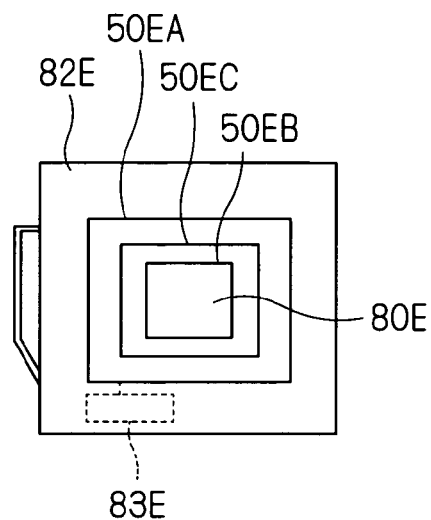
FIG. 29 is a view showing an exemplary case where one cassette is commonly used in a plurality of imaging modes.

This is especially effective in the following case. As shown in FIG. 29, a cassette which can be used commonly for all the CT imaging modes (the x-ray CT imaging mode for large radiation field, the x-ray CT imaging mode for small radiation field and the x-ray CT imaging mode for medium radiation field) can be adopted as a cassette 82E. Specifically, if an x-ray image sensor 80E provided in the cassette 82E has a detection surface with extension which allows detection of the x-ray in all the CT imaging modes, the cassette 82E can be used commonly for all the CT imaging modes. More specifically, as shown in FIG. 29, the detection surface of the x-ray image sensor 80E has extension wider than any one of a radiation region 50EA for the x-ray in the x-ray CT imaging mode for large radiation field, a radiation region 50EB for the x-ray in the x-ray CT imaging mode for small radiation field and a radiation region 50EC for the x-ray in the x-ray CT imaging mode for medium radiation field. Further, the cassette 82E has an information processing part 83E for outputting information indicating that this is a cassette used commonly for all the CT imaging modes. When the cassette 82E is inserted, by individually inputting specification of the CT imaging mode (one of the x-ray CT imaging mode for large radiation field, the x-ray CT imaging mode for small radiation field and the x-ray CT imaging mode for medium radiation field) to be performed, the changed imaging object region display RA, RB, RC, CSA, CSB or CSC can be displayed.

Further, by using an image obtained by actual radiography of the object, such as the above panoramic x-ray image, as the position setting image, the imaging object region display can be specified relatively precisely.

Figure 33:
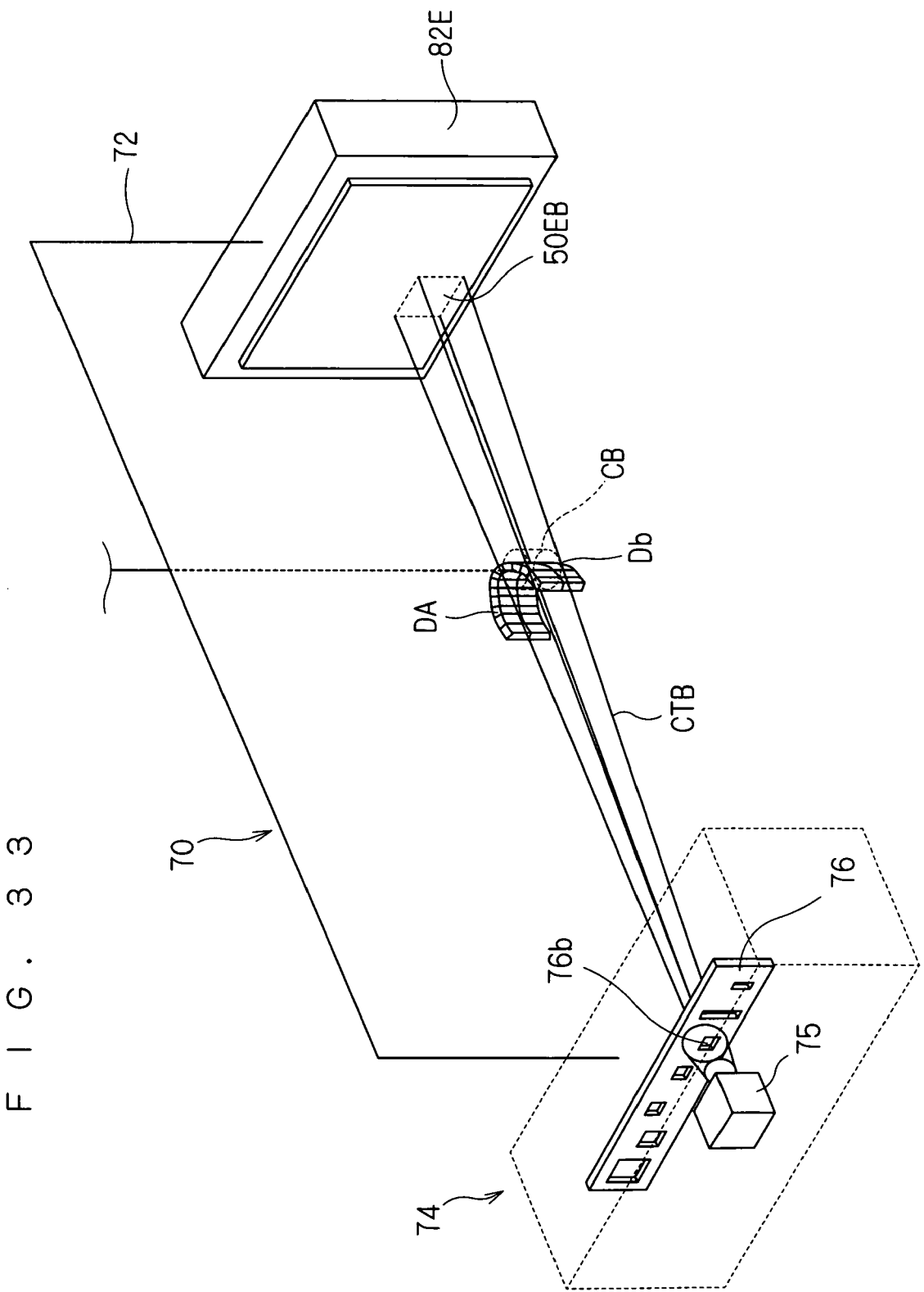
FIG. 33 is a view showing an exemplary case where the x-ray CT is performed in the x-ray CT imaging mode for small radiation field by using the cassette of FIG. 29.

FIG. 33 is a view showing an exemplary case where the x-ray CT is performed in the x-ray CT imaging mode for small radiation field by using the cassette 82E shown in FIG. 29.

In the state of FIG. 33, the opening 76*b* which is located lowest among the three openings 76*b* for the x-ray CT of the small radiation field is positioned to the front of the x-ray generator body 75 in the radiation direction. Then, the x-ray cone beam CTB for the x-ray CT of the small radiation field is emitted to the object, e.g., the specified tooth Db, and its transmission x-ray is detected by the x-ray image sensor 80E of the cassette 82E.

In this configuration, by moving the shield member 76 to select one of the three openings 76b for the x-ray CT of the small radiation field as appropriate, the radiation direction of the x-ray cone beam CTB can be changed up and down in this figure. For example, when it is intended to perform radiography of the tooth of the lower jaw, the lowest opening 76b is selected out of the three openings 76b and an upward x-ray cone beam CTB is emitted to the object, and when it is intended to perform radiography of the tooth of the upper jaw, the highest opening 76b is selected and a downward x-ray cone beam CTB is emitted to the object.

Figure 34:
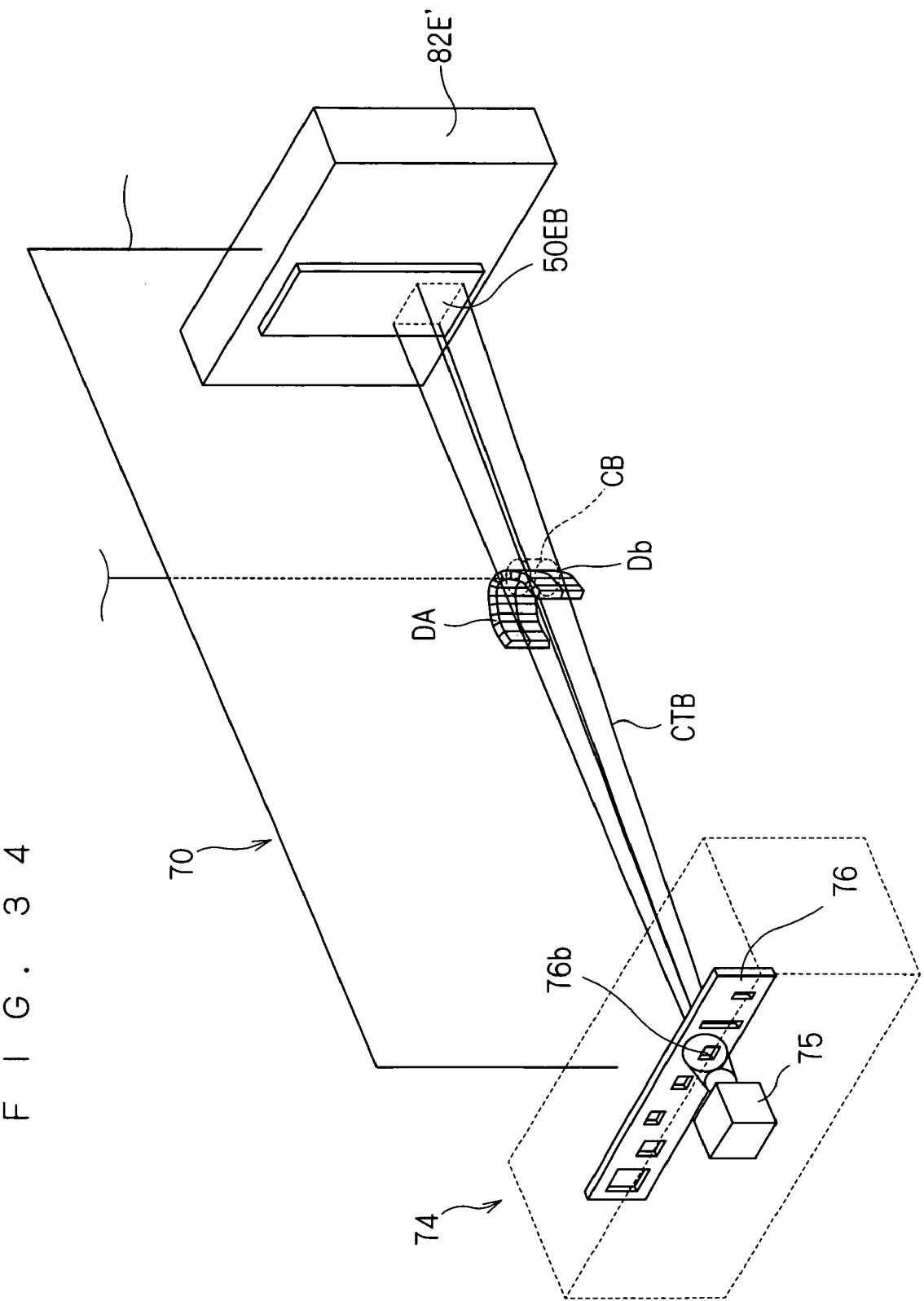
FIG. 34 is a view showing an exemplary case of using a cassette in accordance with the variation of the cassette shown in FIG. 33.

FIG. 34 shows an exemplary case of using a cassette 82E' in accordance with the variation of the cassette 82E shown in FIG. 33. The cassette 82E' is different from the cassette 82E in that the width of the detection surface of the x-ray image sensor 80E' in the cassette 82E' is set the same as that of the x-ray image sensor 80B in the cassette 82B of FIG. 6. Also in this configuration, like in the configuration of FIG. 33, by moving the shield member 76 to select one of the three openings 76b for the x-ray CT of the small radiation field as appropriate, the radiation direction of the x-ray cone beam CTB can be changed up and down in this figure.

<Variations>

Though a plurality of imaging modes are the x-ray CT imaging mode for large radiation field, the x-ray CT imaging mode for small radiation field and the x-ray CT imaging mode for medium radiation field in the above preferred embodiment, the imaging mode is not limited to these exemplary modes but x-ray CT imaging modes with x-ray CT imaging regions of different shapes may be adopted.

Further, though the dental arch image schematically representing a general row of teeth and the panoramic x-ray image obtained by performing panoramic radiography of the object in advance are used as the position setting image in the preferred embodiment, the position setting image is not limited to these exemplary images.

Figure 30:
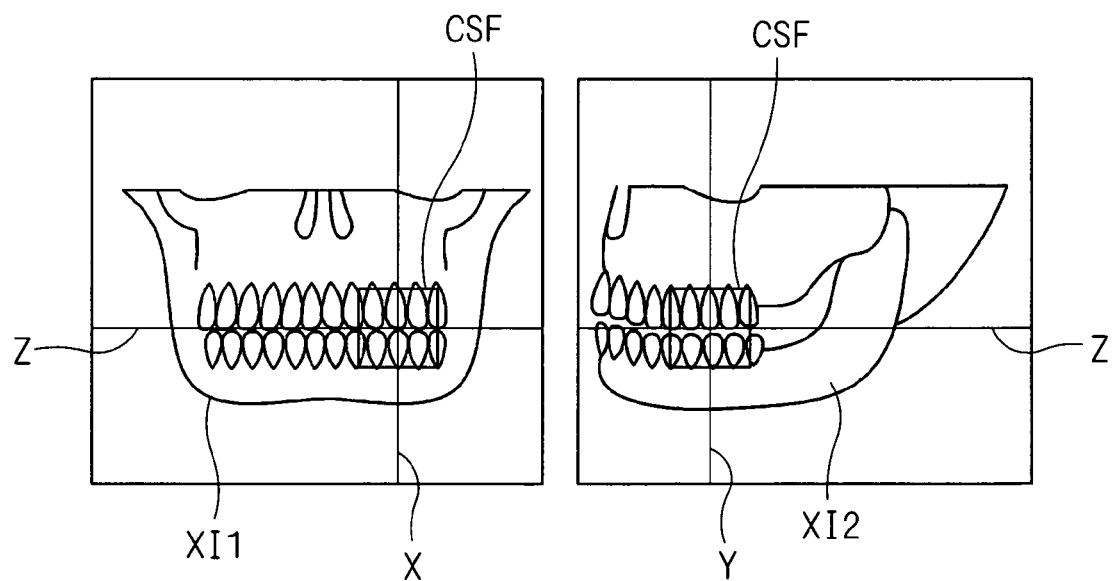
FIG. 30 is a view showing an exemplary position setting screen using a plurality of x-ray transmission images obtained by performing radiography of an object from various angles as position setting images.

As shown in FIG. 30, for example, a plurality of x-ray transmission images obtained by radiography of the object from different angles may be adopted. In FIG. 30, an x-ray transmission image XI1 obtained by radiography of the row of teeth as the object from its front and an x-ray transmission image XI2 obtained by radiography of the row of teeth as the object from its side are used as the position setting images, and images obtained by superposing an imaging object region display CSF in accordance with the imaging mode (herein, the imaging mode for small radiation field) on these images XI1 and XI2 are displayed. Further, together with the imaging object region display CSF, the X axis, the Y axis and the Z axis with the central point of the imaging object region display CSF as the center are displayed.

Alternatively, the position setting image may be a stereographic image representing the whole row of teeth. In summary, as the position setting image, any image presenting a whole or part of an imaging object which is a target to the operator may be adopted, regardless of whether obtained by an actual radiography or not or of which mode of the radiography.

Though the exemplary displays of substantially circular shape and substantially quadrate shape are proposed as the imaging object region display, the imaging object region display is not limited to have these shapes. As the imaging object region display, for example, part of substantially circular shape and part of substantially quadrate shape (e.g., four substantially L-shaped marks representing the vertices of a substantially quadrate frame, only a pair of opposed sides or the like), cross-like marks or a radiate mark like "*" may be adopted, and these may be indicated by dotted lines, broken lines or the like. If the stereographic image or the like is used as the position setting image, a display of substantially cylinder-like shape may be adopted. In summary, any display representing the imaging object region in accordance with the imaging mode on the position setting image may be adopted.

Further, when the position of the imaging object region is set with respect to the above position setting image, the imaging object region may be moved with respect to the fixed position setting image or the position setting image may be moved while the imaging object region is fixed.

Figure 31:
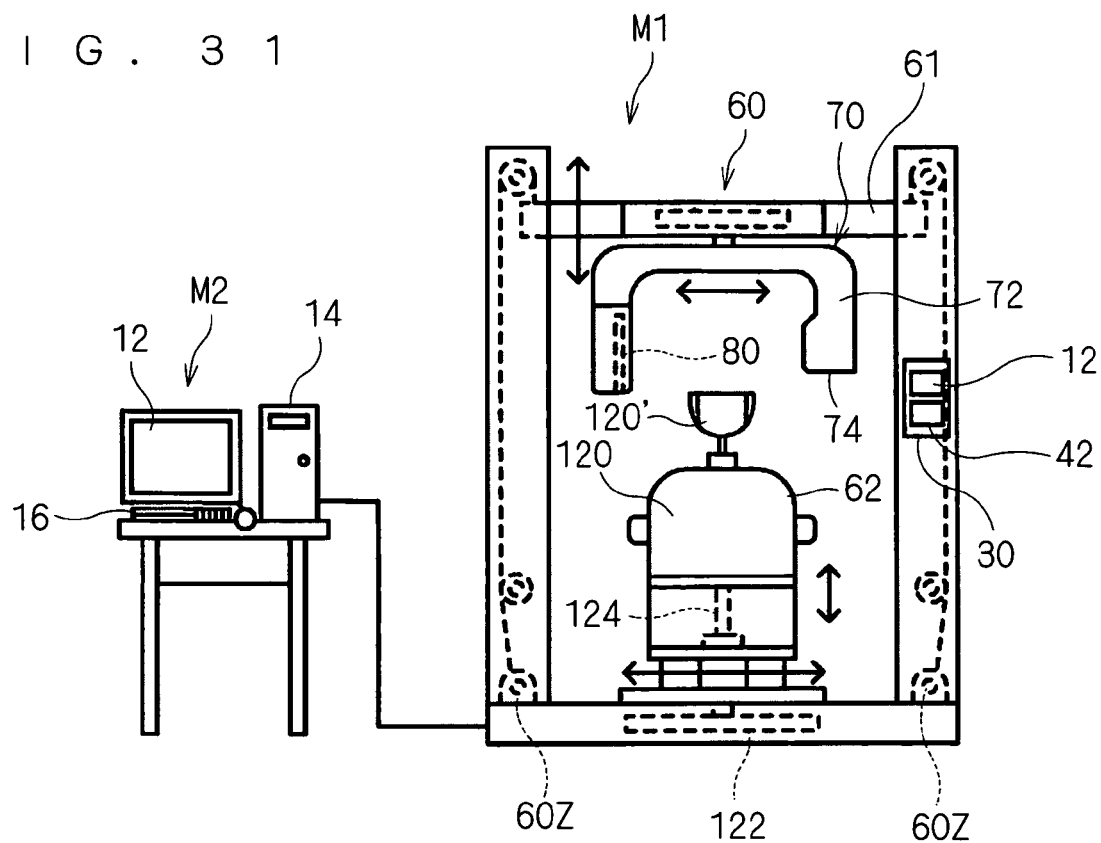
FIG. 31 is a view showing a variation where the object is moved.
Figure 32:
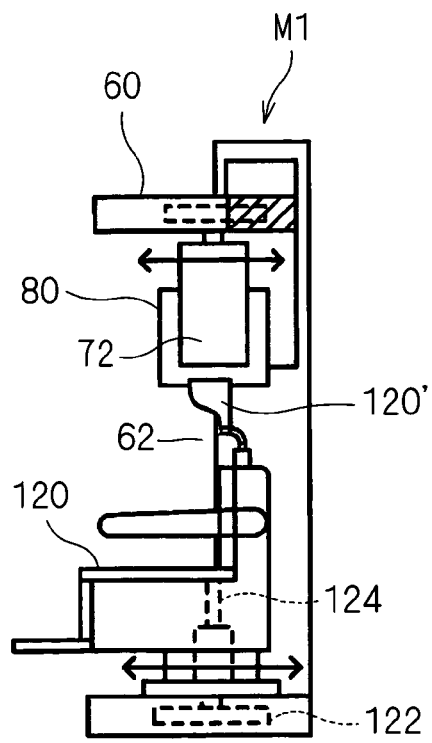
FIG. 32 is a view showing a variation where the object is moved.

Though the configuration to move the x-ray image sensor 80 and the x-ray generator 74 by the moving mechanism part 60 is discussed in the preferred embodiment, the x-ray image sensor 80 and the x-ray generator 74 have only to be moved relatively to the object. As shown in FIGS. 31 and 32, for example, in a state where a patient which is an imaging object is sitting on a chair 120, the chair 120 may be moved by a vertical moving mechanism part 124 and a horizontal moving mechanism part 122.

The chair 120 holds the object, serving as the holding part 62. In order to secure the head, it is preferable to provide a headrest 120' as shown in these figures. The horizontal moving mechanism part 122 and the vertical moving mechanism part 124 constitute the moving mechanism part 60 on the side of the holding part discussed with reference to FIG. 1. The horizontal moving mechanism part 122 is an X-Y moving mechanism part and consists of the X-axis motor 60x and the Y-axis motor 60y described above. The vertical moving mechanism part 124 is a Z moving mechanism part and formed of the above-described Z-axis motor 60z. In FIGS. 31 and 32, the constituent elements identical to those in the above preferred embodiment are represented by the same reference signs.

Though discussion is made in the preferred embodiment on the case where the imaging object is human teeth, the imaging object is not limited to this example. For example, the imaging object may be a whole head, an ear, a nose, an eye or the like. Further, the imaging object is not limited to human body parts but may be parts of body of a small animal such as a dog, a cat or the like, parts of body of a larger animal, or the like.

Therefore, the imaging object is not limited to teeth in dental arch and tusks but may be a maxillary sinus portion, tissues around a stapes which are important portions to be examined in otolaryngology, or tissues around an eyeball which are important portions to be examined in ophthalmology. Further, in the industrial CT, the present invention can be applied to a case of examining detailed structure of each portion of a product or its part.

Though discussion is made in the preferred embodiment on the case where the dental arch image schematically representing the dental arch is used as the position setting image schematically representing a tissue, the position setting image may be an image schematically representing a maxillary sinus portion and tissues around it, an image schematically representing an ear and tissues around it, or an image schematically representing an eyeball and tissues around it.

Though the type in which the radiography is performed while a patient who is an object is standing is shown in the preferred embodiment, the present invention is not limited to this type but can be applied to a type in which the radiography is performed while a patient is lying, with the rotation axis of the imaging unit body provided in the horizontal direction.

Though discussion is made in the preferred embodiment on the case where the cassette 82 is interchanged in accordance with the imaging mode, the present invention is not limited to this configuration to make the cassette removable for the interchange. There may be a configuration, for example, where a plurality of cassettes 82 are provided movably with respect to a position opposed to the x-ray generator 74 and switching is made to bring one of the cassettes 82 to the position opposed to the x-ray generator 74. Then, the cassette 82 which is brought to the position opposed to the x-ray generator 74 outputs a signal in accordance with its own imaging mode.

Further, the configuration to detect the imaging mode of the cassette 82 is not limited to the above-discussed configuration in which the information processing part 83 outputs a signal indicating its own type. For example, each cassette 82 may be provided with an IC (Integrated Circuit) chip dedicated to output of the signal indicating its own type. Furthermore, there may be a configuration where a reader provided in the cassette holder 72a reads optical information (bar code and the like) or magnetic information (magnetic stripe and the like) affixed to each cassette 82, to select the imaging mode in accordance with the type of the cassette. There may be another configuration where the cassettes 82 are provided with different patterns of pits and projections and a microswitch, a photosensor or the like provided in the cassette holder 72a outputs a signal corresponding to the pattern of pits and projections as the signal indicating the imaging mode.

Since the imaging unit body 70 has only to be moved relatively to the object, it is possible that the moving mechanism part 60 can have various aspects including the above exemplary aspect, such as the following combinations.

Aspect A: The holding part 62 has the X-Y moving mechanism part (the part of the moving mechanism part 60 on the side of the holding part) for moving the holding part 62 in the X-axis direction and the Y-axis direction, and the imaging unit body 70 has no X-Y moving mechanism part (the part of the moving mechanism part 60 on the side of the imaging unit body). The imaging unit body 70 does not move in the X-axis direction or the Y-axis direction and the holding part 62 moves in the X-axis direction and the Y-axis direction. Preferably, at least one of the imaging unit body 70 and the holding part 62 moves in the Z-axis direction.

Aspect B: The imaging unit body 70 has the X-Y moving mechanism part (the part of the moving mechanism part 60 on the side of the imaging unit body) for moving the imaging unit body 70 in the X-axis direction and the Y-axis direction, and the holding part 62 has no X-Y moving mechanism part (the part of the moving mechanism part 60 on the side of the holding part). The imaging unit body 70 moves in the X-axis direction and the Y-axis direction and the holding part 62 does not move in the X-axis direction or the Y-axis direction. Preferably, at least one of the imaging unit body 70 and the holding part 62 moves in the Z-axis direction.

Aspect C: The holding part 62 has a moving mechanism part (the part of the moving mechanism part 60 on the side of the holding part) for moving the holding part 62 in the X-axis direction, and the imaging unit body 70 has a moving mechanism part (the part of the moving mechanism part 60 on the side of the imaging unit body) for moving the imaging unit body 70 in the Y-axis direction. The holding part 62 moves in the X-axis direction and the imaging unit body 70 moves in the Y-axis direction. The total movements of the holding part 62 and the imaging unit body 70 allow the imaging unit body 70 to move two-dimensionally in the horizontal plane with respect to the object. Preferably, at least one of the imaging unit body 70 and the holding part 62 moves in the Z-axis direction.

Aspect D: The holding part 62 has a moving mechanism part (the part of the moving mechanism part 60 on the side of the holding part) for moving the holding part 62 in the Y-axis direction, and the imaging unit body 70 has a moving mechanism part (the part of the moving mechanism part 60 on the side of the imaging unit body) for moving the imaging unit body 70 in the X-axis direction. The holding part 62 moves in the Y-axis direction and the imaging unit body 70 moves in the X-axis direction. The total movements of the holding part 62 and the imaging unit body 70 allow the imaging unit body 70 to move two-dimensionally in the horizontal plane with respect to the object. Preferably, at least one of the imaging unit body 70 and the holding part 62 moves in the Z-axis direction.

Though the above exemplary aspects A to D focus attention on the moving mechanisms in the X-axis direction and the Y-axis direction, since the present invention has only to move the imaging unit body 70 two-dimensionally in the horizontal plane with respect to the object, a configuration, for example, where the rotation axis of the above imaging unit body 70 is provided in a disc-like rotation member at a portion out of its rotation center and the rotation axis is moved two-dimensionally in the horizontal plane or a configuration where the rotation axis of the imaging unit body 70 is provided at a tip of a plurality of arm members connected to one another with rotating joints and the rotation axis is moved two-dimensionally in the horizontal plane may be adopted.

Further, a configuration where a moving mechanism is provided but only part of it is driven for movement control may be adopted. There may be a case, for example, where each of the part of the moving mechanism part 60 on the side of the holding part and the part of the moving mechanism part 60 on the side of the imaging unit body consists of the X-Y moving mechanism part and the Z moving mechanism part but the part of the moving mechanism part 60 on the side of the holding part controls only the movement in the X-axis direction and the moving mechanism part 60 on the side of the imaging unit body controls only the movement in the Y-axis direction.

The movement of the imaging unit body 70 relative to the object allows the x-ray generator 74 and the x-ray image sensor 80 to move relatively to the object. In the present invention, the movement of the imaging unit body 70 relative to the object includes all the cases where the object is moved while the imaging unit body 70 is kept still, where the imaging unit body 70 is moved while the object is kept still and where both the imaging unit body 70 and the object are moved simultaneously or alternately.

While the x-ray CT imaging apparatus of the present invention has been shown and described in detail, the foregoing description is in all aspects. illustrative and the invention is not restricted thereto. It is therefore understood that numerous modifications and variations can be devised without departing from the scope of the invention.

The invention claimed is:

1. An x-ray CT imaging apparatus for emitting an x-ray cone beam to an object to generate an x-ray CT image on the basis of a transmission x-ray which is transmitted through the object, comprising:
   an x-ray generator;
   an x-ray image sensor provided oppositely to said x-ray generator with said object interposed there between, for outputting x-ray projection data in accordance with a transmission x-ray which is transmitted through said object;
   an imaging mode selection part for selecting a mode from a plurality of x-ray CT imaging modes with x-ray CT imaging regions of different shapes;
   an image generation part for generating an x-ray CT image in accordance with the x-ray CT imaging mode selected by said imaging mode selection part on the basis of the x-ray projection data outputted from said x-ray image sensor and for generating an image obtained by superposing an imaging object region display on a position setting image representing said object;

an operation part for receiving an operation for moving said imaging object region display relatively to said position setting image;

a moving mechanism part for positioning said x-ray generator and said x-ray image sensor relatively to said object in accordance with the position of said imaging object region display; and a display part for displaying an image generated by said image generation part, wherein said image generation part changes said imaging object region display in accordance with which of the plurality of x-ray CT imaging modes is selected by said imaging mode selection part.

2. The x-ray CT imaging apparatus according to claim 1, wherein said imaging mode selection part receives a setting command for said x-ray CT imaging mode given by an operator to select said x-ray CT imaging mode.

3. The x-ray CT imaging apparatus according to claim 1, wherein said plurality of x-ray CT imaging modes include a local x-ray CT imaging mode.

4. The x-ray CT imaging apparatus according to claim 1, wherein said position setting image is at least one of a dental arch image schematically representing a dental arch, a panoramic x-ray image obtained by panoramic radiography of the object and a plurality of x-ray transmission images obtained by performing radiography of said object from various angles.

5. An x-ray CT imaging apparatus for emitting an x-ray cone beam to an object to generate an x-ray CT image on the basis of a transmission x-ray which is transmitted through the object, comprising:

an x-ray generator;

an x-ray image sensor provided oppositely to said x-ray generator with said object interposed there between interchangeably or switchably, for outputting x-ray projection data in accordance with a transmission x-ray which is transmitted through said object;

a mode signal output part for outputting an imaging mode signal for one of a plurality of x-ray CT imaging modes with x-ray CT imaging regions of different shapes, in accordance with the interchange or switch of said x-ray image sensor;

an image generation part for generating an x-ray CT image in accordance with the x-ray CT imaging mode selected by said imaging mode signal on the basis of the x-ray projection data outputted from said x-ray image sensor and for generating an image obtained by superposing an imaging object region display on a position setting image representing said object;

an operation part for receiving an operation for moving said imaging object region display relatively to said position setting image;

a moving mechanism part for positioning said x-ray generator and said x-ray image sensor relatively to said object in accordance with the position of said imaging object region display; and a display part for displaying an image generated by said image generation part, wherein said image generation part changes said imaging object region display in accordance with which of the plurality of x-ray CT imaging modes is selected by said imaging mode signal.

6. The x-ray CT imaging apparatus according to claim 5, wherein said plurality of x-ray CT imaging modes include a local x-ray CT imaging mode.

7. The x-ray CT imaging apparatus according to claim 5, wherein said position setting image is at least one of a dental arch image schematically representing a dental arch, a panoramic x-ray image obtained by panoramic radiography of the object and a plurality of x-ray transmission images obtained by performing radiography of said object from various angles.

* * * * *